(12) United States Patent
Mayse

(10) Patent No.: US 10,869,997 B2
(45) Date of Patent: *Dec. 22, 2020

(54) METHODS FOR IMPROVING DRUG EFFICACY

(71) Applicant: Nuvaira, Inc., Plymouth, MN (US)

(72) Inventor: Martin L. Mayse, Wayzata, MN (US)

(73) Assignee: Nuvaira, Inc., Plymouth, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/191,603

(22) Filed: Jun. 24, 2016

(65) Prior Publication Data

US 2017/0050008 A1 Feb. 23, 2017

Related U.S. Application Data

(63) Continuation of application No. 14/142,350, filed on Dec. 27, 2013, now Pat. No. 9,398,933.

(Continued)

(51) Int. Cl.
| | |
|---|---|
| *A61M 37/00* | (2006.01) |
| *A61B 18/18* | (2006.01) |
| *A61K 31/137* | (2006.01) |
| *A61K 31/522* | (2006.01) |
| *A61K 31/56* | (2006.01) |
| *A61K 31/573* | (2006.01) |
| *A61K 31/00* | (2006.01) |
| *A61B 17/32* | (2006.01) |
| *A61B 18/14* | (2006.01) |

(Continued)

(52) U.S. Cl.
CPC ............ *A61M 37/00* (2013.01); *A61B 17/32* (2013.01); *A61B 18/1492* (2013.01); *A61B 18/18* (2013.01); *A61K 9/007* (2013.01); *A61K 31/00* (2013.01); *A61K 31/137* (2013.01); *A61K 31/522* (2013.01); *A61K 31/56* (2013.01); *A61K 31/573* (2013.01); *A61K 45/06* (2013.01); *A61N 1/3611* (2013.01); *A61B 2018/0022* (2013.01); *A61B 2018/00023* (2013.01); *A61B 2018/00541* (2013.01); *A61B 2018/00577* (2013.01)

(58) Field of Classification Search
None
See application file for complete search history.

(56) References Cited

U.S. PATENT DOCUMENTS

| | | |
|---|---|---|
| 5,139,029 A | 8/1992 | Fishman et al. |
| 5,496,304 A | 3/1996 | Chasan |

(Continued)

OTHER PUBLICATIONS

Drugs.com 2015 "Second generation cephalosporins" accessed from drugs.com on Jan. 5, 2015.*

(Continued)

*Primary Examiner* — Adam Weidner
(74) *Attorney, Agent, or Firm* — Patterson Thuente Pedersen, P.A.

(57) ABSTRACT

The present disclosure provides methods for improving drug efficacy in a patient having an obstructed airway in a lung. Such methods modulate nerve activity in the autonomic nervous system of a patient to reduce obstruction of an airway in a lung of the patient prior to administering a drug to the patient. These methods are especially useful in improving efficacies of bronchodilators in treating obstructive lung diseases, such as chronic obstructive pulmonary disease.

26 Claims, 5 Drawing Sheets

Related U.S. Application Data

(60) Provisional application No. 61/746,460, filed on Dec. 27, 2012.

(51) Int. Cl.
*A61K 9/00* (2006.01)
*A61K 45/06* (2006.01)
*A61N 1/36* (2006.01)
*A61B 18/00* (2006.01)

(56) References Cited

U.S. PATENT DOCUMENTS

| | | | |
|---|---|---|---|
| 6,726,677 B1 | 4/2004 | Flaherty et al. |
| 7,608,275 B2 | 10/2009 | Deem et al. |
| 8,088,127 B2 | 1/2012 | Mayse et al. |
| 8,133,497 B2 | 3/2012 | Deem et al. |
| 8,172,827 B2 | 5/2012 | Deem et al. |
| 8,226,638 B2 | 7/2012 | Mayse et al. |
| 8,338,164 B2 | 12/2012 | Deem et al. |
| 8,483,831 B1 | 7/2013 | Hlavka et al. |
| 8,489,192 B1 | 7/2013 | Hlavka et al. |
| 8,731,672 B2 | 5/2014 | Hlavka et al. |
| 8,740,895 B2 | 6/2014 | Mayse et al. |
| 8,777,943 B2 | 7/2014 | Mayse et al. |
| 8,808,280 B2 | 8/2014 | Mayse et al. |
| 8,821,489 B2 | 9/2014 | Mayse et al. |
| 8,911,439 B2 | 12/2014 | Mayse et al. |
| 8,932,289 B2 | 1/2015 | Mayse et al. |
| 8,961,507 B2 | 2/2015 | Mayse et al. |
| 8,961,508 B2 | 2/2015 | Mayse et al. |
| 9,005,195 B2 | 4/2015 | Mayse et al. |
| 9,017,324 B2 | 4/2015 | Mayse et al. |
| 9,125,643 B2 | 9/2015 | Hlavka et al. |
| 9,149,328 B2 | 10/2015 | Dimmer et al. |
| 9,339,618 B2 | 5/2016 | Deem et al. |
| 2003/0018344 A1 | 1/2003 | Kaji et al. |
| 2004/0226556 A1 | 11/2004 | Deem et al. |
| 2006/0225742 A1 | 10/2006 | Deem et al. |
| 2009/0155336 A1* | 6/2009 | Rezai ............... A61F 2/82 424/423 |
| 2009/0306644 A1* | 12/2009 | Mayse ............... A61B 8/12 606/33 |
| 2010/0228318 A1* | 9/2010 | Errico ............... A61N 1/3601 607/42 |
| 2011/0118725 A1 | 5/2011 | Mayse et al. |
| 2011/0152855 A1 | 6/2011 | Mayse et al. |
| 2011/0195973 A1* | 8/2011 | Johnson ............... C07D 401/12 514/252.11 |
| 2011/0257647 A1 | 10/2011 | Mayse et al. |
| 2011/0301587 A1 | 12/2011 | Deem et al. |
| 2012/0016358 A1 | 1/2012 | Mayse et al. |
| 2012/0016363 A1 | 1/2012 | Mayse et al. |
| 2012/0016364 A1 | 1/2012 | Mayse et al. |
| 2012/0203216 A1 | 8/2012 | Mayse et al. |
| 2012/0203222 A1 | 8/2012 | Mayse et al. |
| 2012/0209261 A1 | 8/2012 | Mayse et al. |
| 2012/0209296 A1 | 8/2012 | Mayse et al. |
| 2012/0302909 A1 | 11/2012 | Mayse et al. |
| 2012/0310233 A1 | 12/2012 | Dimmer et al. |
| 2012/0316552 A1 | 12/2012 | Mayse et al. |
| 2012/0316559 A1 | 12/2012 | Mayse et al. |
| 2013/0123751 A1 | 5/2013 | Deem et al. |
| 2013/0289555 A1 | 10/2013 | Mayse et al. |
| 2013/0289556 A1 | 10/2013 | Mayse et al. |
| 2013/0296647 A1 | 11/2013 | Mayse et al. |
| 2013/0303948 A1 | 11/2013 | Deem et al. |
| 2013/0310822 A1 | 11/2013 | Mayse et al. |
| 2013/0345700 A1 | 12/2013 | Hlavka et al. |
| 2014/0186341 A1 | 7/2014 | Mayse |
| 2014/0236148 A1 | 8/2014 | Hlavka et al. |
| 2014/0257271 A1 | 9/2014 | Mayse et al. |
| 2014/0276792 A1 | 9/2014 | Kaveckis et al. |
| 2015/0051597 A1 | 2/2015 | Mayse et al. |
| 2015/0141985 A1 | 5/2015 | Mayse et al. |
| 2015/0190193 A1 | 7/2015 | Mayse et al. |
| 2015/0366603 A1 | 12/2015 | Hlavka et al. |
| 2016/0022351 A1 | 1/2016 | Kaveckis et al. |
| 2016/0038725 A1 | 2/2016 | Mayse et al. |

OTHER PUBLICATIONS

Gershon 2011 "comparison of inhaled long-acting .beta.agonist and anticholinergic effectiveness in older patients with chronic obstructive pulmonary disease" Ann Int Med 154(9):583-592/w-203-w-215.*

Gorny 1977 "The effect of adrenaline on acetylcholine synthesis after blockade of alpha and beta adrenergic receptors in vitro" acta physiol pol 28(4):313-20.*

Application and File History of U.S. Appl. No. 14/142,350; Inventors: Mayse; filed Dec. 27, 2013.

Coenraad Frederik N. Koegelenberg, et al., "Antimuscarinic Bronchodilator Response Retained after Bronchoscopic Vagal Denervation in Chronic Obstructive Pulmonary Disease Patients", Jun. 30, 2016, 3 pages.

* cited by examiner

METHODS FOR IMPROVING DRUG EFFICACY

RELATED APPLICATIONS

This application is a continuation of U.S. application Ser. No. 14/142,350 filed Dec. 27, 2013, which claims the benefit of U.S. Provisional Application No. 61/746,460 filed Dec. 27, 2012, each of which is incorporated herein in its entirety by reference.

TECHNICAL FIELD

The present disclosure relates to methods for improving drug efficacy in patients having obstructed airways of the lungs.

DESCRIPTION OF THE RELATED ART

Pulmonary diseases are disorders that affect the lungs. Pulmonary diseases, such as asthma and chronic obstructive pulmonary disease ("COPD"), may lead to increased airflow resistance in the lungs. Mortality, health-related costs, and the size of the population having adverse effects due to pulmonary diseases are all substantial. These diseases often adversely affect quality of life. Symptoms are varied but often include coughing, breathlessness, and wheezing. In COPD, for example, breathlessness may be noticed when performing somewhat strenuous activities, such as running, jogging, brisk walking, etc. As the disease progresses, breathlessness may be noticed when performing non-strenuous activities, such as walking. Over time, symptoms of COPD may occur with less and less effort until they are present all of the time, thereby severely limiting a person's ability to accomplish normal tasks.

Many measures have been taken to treat or manage pulmonary diseases. For example, for COPD, bronchodilators, corticosteroids, and other medications may be administered to patients with COPD. In addition, supplemental oxygen, and pulmonary rehabilitation may also be used to treat or manage COPD. Furthermore, many pharmacological-based treatment options focus on the vagus nerve, which innervates the conducting airways from the trachea to the terminal bronchioles.

Treatment options that prevent or inhibit the production and/or the release of acetylcholine are also of great interest. For example, parasympathetic nerves provide the dominant autonomic innervation of the airways. Release of acetylcholine from parasympathetic nerves activates postjunctional muscarinic receptors present on airway smooth muscle, submucosal glands, and blood vessels to cause bronchoconstriction, mucus secretion, and vasodilatation, respectively. Acetylcholine also feeds back onto prejunctional muscarinic receptors to enhance or inhibit further acetylcholine release. In asthma and COPD, bronchoconstriction and mucus secretion is increased and the airways are hyperresponsive to contractile agents. These changes are not due to increased parasympathetic nerve activity, as the number and function of postjunctional muscarinic receptors in the airways are generally unchanged. Rather, it is the supply of acetylcholine to the postjunctional cells (smooth muscle and submucosal gland) that is increased. Therefore, preventing the release or production of acetylcholine to the postjunctional cells remains a promising treatment option.

Treatment options that block the binding of acetylcholine to its receptor in nerve cells are also of great interest. For example, stimulation of the vagus nerves can cause the release of acetylcholine and leads to bronchoconstriction, as described above. Although lung cholinergic pathways are highly complicated as recognized by one of ordinary skill in the art, in its simplest form, preganglion fibers release acetylcholine at the level of peribronchial ganglia, from which postganglion fibers are generated, leading to the release of acetylcholine in the bronchial wall. The muscarinic (M) receptors activated by the release of acetylcholine and involved in the airway tone regulation, as described above, include: M1 receptors, present on the cholinergic ganglia, with the role of facilitating neural transmission; M2 receptors, located on the postganglion endings of the cholinergic fibers, with the role of limiting further acetylcholine release from the postganglion endings; and M3 receptors, located on the smooth muscle cells, mucosal glands and vascular endothelium in the airway wall, then inducing bronchoconstriction, mucus hypersecretion and airway wall edema. Therefore, the release of acetylcholine leads to the stimulation of the airway smooth muscle and of the mucous bronchial glands in the airways via activation of the receptors, with subsequent bronchoconstriction and mucus secretion, both events causing an increase in airway resistance. This response can be blocked by the administration of anticholinergic agents such as atropine, ipratropium, or the like, which selectively block the binding of acetylcholine to its receptor in nerve cells.

However, currently, there is still no cure for COPD, and individual treatments have not resulted in optimal outcomes. Even combinations of various treatments have been shown to generate minimum improvements over individual treatments. For example, previous studies showed that a combination of two treatments, even if they were based on different mechanisms of action, resulted in substantially less than the additive effect of the two treatments. Matera et al. show that in patients with COPD, addition of ipratropium bromide (an anticholinergic agent) at the clinically recommended dose did not produce any further bronchodilation than that achieved with salmeterol (a beta agonist) or formoterol (a beta agonist) (see, Respir Med 90:497-9, 1996; Sichletidis et al., Int J Clin Pract 53:185-8, 1999). Even when oxitropium bromide (a muscarinic antagonist) was used at a dose higher than the clinically recommended dose, it resulted in a modest improvement in FEV1 (forced expiratory volume in 1 second). For example, Salmeterol caused a 0.25 liter (22%) improvement in FEV1, oxitropium caused a 0.27 liter (23%) improvement in FEV1, and oxitropium taken after salmeterol caused only an additional 0.15 liter (11%) improvement in FEV1 (see, Cazzola et al., Thorax 54:1083-86, 1999).

BRIEF SUMMARY

In one aspect, the present disclosure provides a method for improving efficacy of a drug in a patient having an obstructive lung disease or bronchial constriction in a lung or airway, the drug having a reference efficacy, the method including: (a) modulating nerve activity in the autonomic nervous system of the patient to reduce obstruction in at least one obstructed airway in the lung of the patient, and (b) subsequently administering the drug to the patient, wherein steps (a) and (b) have a treatment efficacy greater than the reference efficacy.

In a related aspect, the present disclosure provides a method for improving drug efficacy in a patient having an obstructive lung disease or bronchial constriction in a lung or airway, the method including administering a drug, wherein the patient has undergone, prior to the administration of the drug, a procedure that modulates or attenuates nerve activity in the autonomic nervous system of the patient to reduce airway obstruction in at least one obstructed airway in a lung of the patient, and wherein a post-treatment efficacy of the drug following said procedure is improved relative to a reference efficacy of the drug.

In another aspect, the present disclosure provides a method for treating a patient having an obstructive lung disease or bronchial constriction in an airway or a lung, the method including: (a) modulating or attenuating nerve activity in the autonomic nervous system of the patient to reduce obstruction in a distal airway in the lung of the patient; and (b) subsequently administering a drug while the obstruction is reduced in the distal airway.

In a related aspect, the present disclosure provides a method for treating a patient having an obstructive lung disease or bronchial constriction in an airway or a lung, the method including: administering a drug to a patient, wherein the patient has undergone a procedure that modulates nerve activity in the autonomic nervous system of the patient to reduce airway obstruction in at least one obstructed airway in a lung of the patient, wherein the drug is administered while the obstruction is reduced in the at least one obstructed airway.

In another aspect, the present disclosure provides a method for treating a patient having an obstructive lung disease or bronchial constriction in an airway or a lung, the method including: (a) administering an inhaled drug to a patient of obstructive pulmonary disease, wherein the patient has previously undergone a procedure comprising: (i) positioning a treatment device in a first airway of the patient, and (ii) delivering energy from the treatment device into a wall of the first airway to reduce airway obstruction in a second airway that is a higher generation airway than the first airway.

In another aspect, the present disclosure provides a method for treating a patient having an obstructive lung disease or bronchial constriction in an airway or a lung, the method including: (a) modulating or attenuating nerve activity in the autonomic nervous system of the patient to reduce obstruction in a distal airway in the lung of the patient; and (b) subsequently or simultaneously administering a drug or combination of drugs that inhibits or prevents the production and/or the release of acetylcholine from parasympathetic nerves at the neuromuscular junction and/or selectively blocks the binding of acetylcholine to its receptor in nerve cells (e.g. anticholinergics or antimuscarinics).

In another aspect, the present disclosure provides a method for treating a patient having an obstructive lung disease or bronchial constriction in an airway or a lung, the method including: inhibiting or preventing the binding of acetylcholine with receptors at a neuromuscular junction between a nerve fiber and a muscle cell in a wall of a first airway by inhibiting the release of acetylcholine from the nerve fiber. In some embodiments, inhibiting the release of acetylcholine can comprise injuring, either permanently or temporarily, the nerve fiber proximally of the neuromuscular junction, such as, for example, by ablation. The ablation can be accomplished via delivery of energy from a device positioned in the airway to the targeted nerve fiber. Any of a variety of energy delivery or ablation techniques can also be contemplated, and as used herein, the term "energy" is broadly construed to include, without limitation, thermal energy, cryogenic energy (e.g., cooling energy), electrical energy, acoustic energy (e.g., ultrasonic energy), radio frequency energy, pulsed high voltage energy, mechanical energy, ionizing radiation, optical energy (e.g., light energy), and combinations thereof, as well as other types of energy suitable for treating tissue. By way of example, thermal energy can be used to heat tissue. Mechanical energy can be used to puncture, tear, cut, crush, or otherwise physically damage tissue. In some embodiments, a distal tip of the energy delivery device is adapted to apply pressure to tissue in order to temporarily or permanently damage tissue. Electrical energy is particularly well suited for damaging cell membranes, such as the cell membranes of nerve trunk tissue or other targeted anatomical features. Acoustic energy can be emitted as continuous or pulsed waves, depending on the parameters of a particular application. Additionally, acoustic energy can be emitted in waveforms having various shapes, such as sinusoidal waves, triangle waves, square waves, or other wave forms.

Additionally or alternatively, inhibiting the release of acetylcholine can comprise administration of a drug that inhibits or prevents the production and/or the release of acetylcholine from parasympathetic nerves at the neuromuscular junction. In this embodiment, the corresponding receptors can be open to binding with acetylcholine or blocked to binding via the administration of an anticholinergic agent, for example. In one particular aspect, the method further includes binding an agent, such as an anticholinergic agent, to second receptors at a second neuromuscular junction in a wall of a second airway to inhibit or prevent acetylcholine from binding to second receptors. The second airway can be of a higher generation airway than the first airway. In yet another aspect, the method can further include inhibiting the release of acetylcholine by interrupting the nerve fiber, such as by ablation, along a third airway, such as the left and/or right main bronchi, the first airway being a higher generation than the third airway.

In the following description, any ranges provided herein include all the values in the ranges. It should also be noted that the term "or" is generally employed in its sense including "and/or" (i.e., to mean either one, both, or any combination thereof of the alternatives) unless the content clearly dictates otherwise. Also, as used in this specification and the appended claims, the singular forms "a," "an," and "the" include plural referents unless the content clearly dictates otherwise. Thus, for example, reference to "an obstructed airway" may refer to one or more obstructed airway.

DETAILED DESCRIPTION

Figure 1:
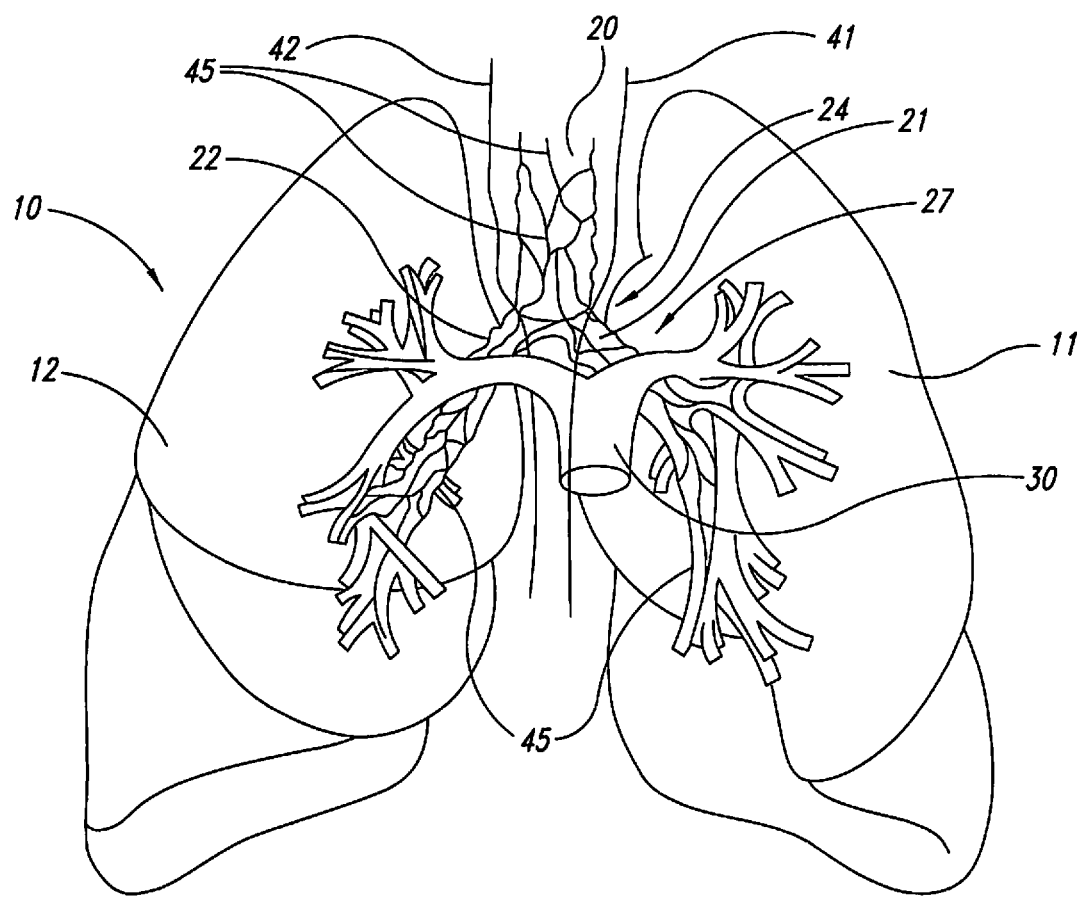
FIG. 1 is an illustration of lungs, blood vessels and nerves near and in the lungs.

FIG. 1 illustrates human lungs 10 having a left lung 11 and a right lung 12. A trachea 20 extends downwardly from the nose and mouth and divides into a left main bronchus 21 and a right main bronchus 22. The left main bronchus 21 and right main bronchus 22 each branch to form lobar bronchi, segmental bronchi, and sub-segmental bronchi, which have successively smaller diameters and shorter lengths in the outward direction (i.e., the distal direction). A main pulmonary artery 30 originates at a right ventricle of the heart and passes in front of a lung root 24. At the lung root 24, the artery 30 branches into a left and a right pulmonary artery, which in turn branch to form a network of branching blood vessels. These blood vessels can extend alongside airways of a bronchial tree 27. The bronchial tree 27 includes the left main bronchus 21, the right main bronchus 22, bronchioles, and alveoli. Vagus nerves 41, 42 extend alongside the trachea 20 and branch to form nerve trunks 45.

The left and right vagus nerves 41, 42 originate in the brainstem, pass through the neck, and descend through the chest on either side of the trachea 20. The vagus nerves 41, 42 spread out into nerve trunks 45 that include the anterior and posterior pulmonary plexuses that wrap around the trachea 20, the left main bronchus 21, and the right main bronchus 22. The nerve trunks 45 also extend along and outside of the branching airways of the bronchial tree 27. Nerve trunks 45 are the main stem of a nerve, comprising a bundle of nerve fibers bound together by a tough sheath of connective tissue.

The primary function of the lungs 10 is to exchange oxygen from air into the blood and to exchange carbon dioxide from the blood to the air. The process of gas exchange begins when oxygen rich air is pulled into the lungs 10. Contraction of the diaphragm and intercostal chest wall muscles cooperate to decrease the pressure within the chest to cause the oxygen rich air to flow through the airways of the lungs 10. For example, air passes through the mouth and nose, the trachea 20, then through the bronchial tree 27. The air is ultimately delivered to the alveolar air sacs for the gas exchange process.

Oxygen poor blood is pumped from the right side of the heart through the pulmonary artery 30 and is ultimately delivered to alveolar capillaries. This oxygen poor blood is rich in carbon dioxide waste. Thin semi-permeable membranes separate the oxygen poor blood in capillaries from the oxygen rich air in the alveoli. These capillaries wrap around and extend between the alveoli. Oxygen from the air diffuses through the membranes into the blood, and carbon dioxide from the blood diffuses through the membranes to the air in the alveoli. The newly oxygen-enriched blood then flows from the alveolar capillaries through the branching blood vessels of the pulmonary venous system to the heart. The heart pumps the oxygen-rich blood throughout the body. The oxygen spent air in the lung is exhaled when the diaphragm and intercostal muscles relax and the lungs and chest wall elastically return to the normal relaxed states. In this manner, air can flow through the branching bronchioles, the bronchi 21, 22, and the trachea 20 and is ultimately expelled through the mouth and nose.

In the first aspect, the present disclosure provides a method for improving drug efficacy in a patient having an obstructive lung disease. Such a method comprises: (a) modulating or attenuating nerve activity in the autonomic nervous system of a patient to reduce obstruction in at least one obstructed airway in the lung of the patient, and (b) subsequently administering the drug to the patient, wherein steps (a) and (b) have a treatment efficacy greater than a reference efficacy of the drug.

The present inventor discovered that reducing obstruction of obstructed airways in lungs of patients having an obstructive lung disease (e.g., COPD) by modulating or attenuating nerve activity in the autonomic nervous system of the patients (e.g., by parasympathetic (vagus) nervous system disruption) followed by administration of a drug (e.g., a bronchodilator or short-acting anticholinergic agents) significantly improved pulmonary functions of the patient.

In one particular example, such an additive effect of administering ipratropium, an anticholinergic agent, after vagus nerve disruption was unexpected. First, because vagus nerve disruption reduces or eliminates acetylcholine production by vagus nerve, and because acetylcholine is required for ipratropium to function as a bronchodilator, one would not expect administration of ipratropium after vagus nerve disruption to significantly improve lung functions. Second, previous studies showed that a combination of two treatments, even if they were based on different mechanisms of action, resulted in substantially less than the additive effect of the two treatments (see, Matera et al., Respir Med 90:497-9, 1996; Sichletidis et al., Int J Clin Pract 53:185-8, 1999; Cazzola et al., Thorax 54:1083-86, 1999). For two treatments with similar mechanisms of action (e.g., vagus nerve disruption that eliminates or reduces acetylcholine production and pharmacological inhibition of acetylcholine production or release), one would expect that the combination of such treatments would result in less of an improvement than the combination of two treatments with different/complementary mechanisms of action.

For simplicity, a treatment that modulates or attenuates nerve activity in the autonomic nervous system of a patient having an obstructive lung disease to reduce obstruction in at least one obstructed airway in a lung of the patient is referred to herein as a "nerve activity-modulating treatment."

A "reference efficacy" of a drug, as used herein, refers to an improvement in a symptom or a parameter associated with a symptom of a patient or a group of patients resulting from administration of the drug or combination of drugs relative to a baseline of the symptom or the parameter associated with the symptom of the patient(s) before the administration of the drug(s) to the patient(s), wherein the patient or the group of patients have not previously undergone a nerve activity-modulating treatment.

A "parameter associated with a symptom" refers to a parameter that may be measured or monitored to determine changes in the symptom. For example, a symptom of COPD is shortness of breath. FEV1 (the forced expiratory volume in 1 second) may be used as a parameter to determine the improvement or deterioration of the symptom of shortness of breath.

In certain embodiments, the patient from whom a reference efficacy of a drug is obtained is the same patient who is subsequently subjected to a nerve activity-modulating treatment. In certain other embodiments, the reference efficacy of a drug is obtained from a patient or a group of patients other than the patient who is subjected to a nerve activity-modulating treatment.

The term "treatment efficacy" of steps (a) and (b), as used herein, refers to a final improvement in a symptom or a parameter associated with a symptom of a patient resulting from step (a) (i.e., a nerve activity-modulating treatment) and step (b) (i.e., administration of the drug subsequent to the nerve activity-modulating treatment) relative to a baseline of the symptom or the parameter associated with the symptom before the patient has been subjected to either the nerve activity-modulating treatment or the administration of the drug.

"Improving efficacy of a drug" in a patient refers to an improvement of the treatment efficacy of steps (a) and (b) over a reference efficacy of the drug used in step (b).

In certain embodiments, similar to the nerve activity-modulating treatment in step (a), the drug administered in step (b) (e.g., bronchodilators) also reduces obstruction in obstructed airways in a lung of a patient. In such cases, the drug has a reference efficacy, that is, an improvement in a symptom or a parameter associated with a symptom of a patient resulting from administration of the drug over a baseline before the administration of the drug in the patient; step (a) has a post-modulating efficacy, that is, an improvement in the symptom or the parameter associated with the symptom resulting from step (a) alone over the baseline; and steps (a) and (b) have a treatment efficacy, that is, a final improvement in the symptom or the parameter associated with the symptom resulting from both steps (a) and (b) over the baseline. The post-modulating efficacy of step (a) may be less than, the same as, or more than the reference efficacy of the drug, but is less than the treatment efficacy of steps (a) and (b).

In certain other embodiments, unlike the nerve activity-modulating treatment in step (a), the drug administered in step (b) is effective in treating another symptom other than reducing obstruction in obstructed airways in a lung of a patient. In such cases, step (a) may have a minimum post-modulating efficacy, but the treatment efficacy of steps (a) and (b) is greater than the reference efficacy of the drug.

In certain embodiments, the treatment efficacy of steps (a) and (b) is at least 10%, 15%, 20%, 25%, 30%, 35%, 40%, 45%, 50%, 55%, 60%, 70%, or 75% greater than the reference efficacy of the drug.

In certain embodiments, the drug is a bronchodilator. In some embodiments, the combined effect of the drug and the nerve activity-modulating treatment is substantially additive. For example, the combined effect may be at least 80%-95% (e.g., at least 80%, 85%, 90%, 92%, 94% or 95%) of the sum of the effect of the drug treatment alone and the effect of the nerve activity-modulating treatment alone.

Any appropriate methods known in the art may be used in determining the reference efficacy of a drug, a post-modulation efficacy of a nerve activity-modulating treatment, and/or a final efficacy of both a nerve activity-modulating treatment and administration of the drug. For example, a reference efficacy of a drug useful in treating a lung disease or disorder (e.g., a bronchodilator), a post-modulation efficacy of a nerve activity-modulating treatment, and/or a final efficacy of both a nerve activity-modulating treatment and administration of the drug may be monitored by various pulmonary function tests, exercise capacity and quality of life questionnaires.

Pulmonary function tests involve objective and reproducible measures of basic physiologic lung parameters, such as total airflow, lung volume, and gas exchange. Indices of pulmonary function tests used for the assessment of obstructive pulmonary diseases include the forced expiratory volume in 1 second (FEV1), the forced vital capacity (FVC), the ratio of the FEV1 to FVC, the total lung capacity (TLC), airway resistance and the testing of arterial blood gases. The FEV1 is the volume of air a patient can exhale during the first second of a forceful exhalation which starts with the lungs completely filled with air. The FEV1 is also the average flow that occurs during the first second of a forceful exhalation. This parameter may be used to evaluate and determine the presence and impact of any airway obstruction. The FVC is the total volume of air a patient can exhale during a forceful exhalation that starts with the lungs completely filled with air. The FEV1/FVC is the fraction of all the air that can be exhaled during a forceful exhalation that is exhaled during the first second. A FEV1/FVC ratio less than 0.7 after the administration of at least one bronchodilator defines the presence of COPD. The TLC is the total amount of air within the lungs when the lungs are completely filled and may increase when air becomes trapped within the lungs of patients with obstructive lung disease. Airway resistance is defined as the pressure gradient between the alveoli and the mouth to the rate of air flow between the alveoli and the mouth. Similarly, resistance of a given airway would be defined as the ratio of the pressure gradient across the given airway to the flow through the airway. Arterial blood gases tests measure the amount of oxygen and the amount of carbon dioxide in the blood and are the most direct method for assessing the ability of the lungs and respiratory system to bring oxygen from the air into the blood and to get carbon dioxide from the blood out of the body.

Exercise capacity tests are objective and reproducible measures of a patient's ability to perform activities. A six-minute walk test (6 MWT) is an exercise capacity test in which a patient walks as far as possible over a flat surface in 6 minutes. Another exercise capacity test involves measuring the maximum exercise capacity of a patient. For example, a physician can measure the amount of power the patient can produce while on a cycle ergometer or the time that a patient can maintain a given level of power output. The patient can breathe 30 percent oxygen and the work load can increase by 5-10 watts every 3 minutes.

Quality of life questionnaires assess a patient's overall health and well-being. The St. George's Respiratory Questionnaire is a quality of life questionnaire that includes 75 questions designed to measure the impact of obstructive lung disease on overall health, daily life, and perceived well-being. The efficacy of a treatment for pulmonary diseases can be evaluated using pulmonary function tests, exercise capacity tests, and/or questionnaires. A treatment program can be modified based on the results from these tests and/or questionnaires.

The methods of the present disclosure are particularly useful for improving drug efficacy, improving drug delivery to a lung, and treating patients having an obstructive lung disease.

An "obstructive lung disease" refers to a category of respiratory disease characterized by airway obstruction. It is generally characterized by inflamed and easily collapsible airways, obstruction to airflow, problems exhaling and frequent office visits and hospitalizations. Obstructive lung diseases includes asthma, COPD (including chronic bronchitis and emphysema), bronchiectasis, and cystic fibrosis.

An airway or a portion thereof is "obstructed" if its diameter is smaller than the diameter of a normal airway or a portion thereof or is otherwise restricted. The obstruction of the airway may result from constriction due to smooth muscle contraction of the airway, obstruction from the presence or accumulation of mucous, and thickness of the airway wall due to edema, inflammation or the like.

Patients that may be treated according to the methods of the present disclosure include and are not limited to those suffering from asthma, COPD (including chronic bronchitis and emphysema), bronchiectasis, and cystic fibrosis.

Asthma can be characterized by contraction of airway smooth muscle, smooth muscle hypertrophy, excessive mucus production, mucous gland hypertrophy, and/or inflammation and swelling of airways. These abnormalities are the result of a complex interplay of local inflammatory cytokines (chemicals released locally by immune cells located in or near the airway wall), inhaled irritants (e.g., cold air, smoke, allergens, or other chemicals), systemic hormones (chemicals in the blood such as the anti-inflammatory cortisol and the stimulant epinephrine), local nervous system input (nerve cells contained completely within the airway wall that can produce local reflex stimulation of smooth muscle cells and mucous glands), and the central nervous system input (nervous system signals from the brain to smooth muscle cells and mucous glands carried through the vagus nerve). These conditions often cause widespread temporary tissue alterations and initially reversible airflow obstruction that may ultimately lead to permanent tissue alteration and permanent airflow obstruction that make it difficult for the asthma sufferer to breathe. Asthma can further include acute episodes or attacks of additional airway narrowing via contraction of hyper-responsive airway smooth muscle that significantly increases airflow resistance. Asthma symptoms include recurrent episodes of breathlessness (e.g., shortness of breath or dyspnea), wheezing, chest tightness, and cough.

Emphysema is a type of COPD often characterized by the alteration of lung tissue surrounding or adjacent to the airways in the lungs. Emphysema can involve destruction of lung tissue (e.g., alveoli tissue such as the alveolar sacs) that leads to reduced gas exchange and reduced radial traction applied to the airway wall by the surrounding lung tissue. The destruction of alveoli tissue leaves areas of emphysematous lung with overly large airspaces that are devoid of alveolar walls and alveolar capillaries and are thereby ineffective at gas exchange. Air becomes "trapped" in these larger airspaces. This "trapped" air may cause over-inflation of the lung, and in the confines of the chest restricts the in-flow of oxygen rich air and the proper function of healthier tissue. This results in significant breathlessness and may lead to low oxygen levels and high carbon dioxide levels in the blood. This type of lung tissue destruction occurs as part of the normal aging process, even in healthy individuals. Unfortunately, exposure to chemicals or other substances (e.g., tobacco smoke) may significantly accelerate the rate of tissue damage or destruction. Breathlessness may be further increased by airway obstruction. The reduction of radial traction may cause the airway walls to become "floppy" such that the airway walls partially or fully collapse during exhalation. An individual with emphysema may be unable to deliver air out of their lungs due to this airway collapse and airway obstructions during exhalation.

Chronic bronchitis is a type of COPD that can be characterized by contraction of the airway smooth muscle, smooth muscle hypertrophy, excessive mucus production, mucous gland hypertrophy, and inflammation of airway walls. Like asthma, these abnormalities are the result of a complex interplay of local inflammatory cytokines, inhaled irritants, systemic hormones, local nervous system, and the central nervous system. Unlike asthma where respiratory obstruction may be largely reversible, the airway obstruction in chronic bronchitis is primarily chronic and permanent. It is often difficult for a chronic bronchitis sufferer to breathe because of chronic symptoms of shortness of breath, wheezing, and chest tightness, as well as a mucus producing cough.

Bronchiectasis is a disease state defined by localized, irreversible dilation of part of the bronchia tree caused by destruction of the muscle and elastic tissue. Involved bronchi are dilated, inflamed, and easily collapsible, resulting in airflow obstruction and impaired clearance of secretions. Bronchiectasis is associated with a wide range of disorders, but it usually results from bacterial infections, such as infections caused by the *Staphylococcus* or *Klebsiella* species, or *Bordetella pertussis*.

Cystic fibrosis is an autosomal recessive genetic disorder affecting most critically the lungs, and also the pancreas, liver, intestine. It is characterized by abnormal transport of chloride and sodium across an epithelium, leading to thick, viscous secretions. Lung disorder associated with cysteic fibrosis results from clogging of the airways due to mucus build-up, decreased mucociliary clearance, and resulting inflammation. Inflammation and infection cause injury and structural changes to the lungs, leading to a variety of symptoms. In the early stages, incessant coughing, copious phlegm production, and decreased ability to exercise are common. Many of these symptoms occur when bacteria that normally inhabit the thick mucus grow out of control and cause pneumonia. In later stages, changes in the architecture of the lung further exacerbate difficulties in breathing. In addition to typical bacterial infections, people with cystic fibrosis more commonly develop other types of lung disease, including allergic bronchopulmonary aspergillosis and infection with *Mycobacterium avium* complex.

Other patients having an obstructive lung disease may also benefit from the methods of the present disclosure. A non-inclusive list of other such diseases includes tuberculosis, non-tuberculous mycobacterial infections, sardoidosis, Churg-Strauss syndrome, and allergic bronchopulmonary aspergillosis.

The methods of the present disclosure comprise modulating nerve activity in a portion of the autonomic nervous system of a patient to reduce narrowing of an airway of a lung of the patient. Referring to FIG. 1, the nervous system provides communication between the brain and the lungs using electrical and chemical signals. A network of nerve tissue of the autonomic nervous system senses and regulates activity of the respiratory system and the vasculature system. Nerve tissue includes fibers that use chemical and electrical signals to transmit sensory and motor information from one body part to another. For example, the nerve tissue can transmit motor information in the form of nervous system input, such as a signal that causes contraction of muscles or other responses. The fibers can be made up of neurons. The nerve tissue can be surrounded by connective tissue, i.e., epineurium. The autonomic nervous system includes a sympathetic system and a parasympathetic system. The sympathetic nervous system is largely involved in "excitatory" functions during periods of stress. The parasympathetic nervous system is largely involved in "vegetative" functions during periods of energy conservation. The sympathetic and parasympathetic nervous systems are simultaneously active and generally have reciprocal effects on organ systems. While innervation of the blood vessels originates from both systems, innervation of the airways are largely parasympathetic in nature and travel between the lung and the brain in the right vagus nerve 42 and the left vagus nerve 41.

The lungs are innervated by the anterior and posterior pulmonary plexuses located anterior and posterior to the root of the lungs. They are mixed plexuses containing parasympathetic (vagal) and sympathetic fibers. The filaments from these plexuses accompany the bronchial tubes, supplying efferent fibers to the bronchial muscle and mucous glands and afferent fibers to the bronchial mucous membrane (which may also referred to as mucosa or the epithelium) and probably to the alveoli of the lung. The efferent fibers of parasympathetic fibers (vagus nerve) are motors to the smooth muscle of the bronchial tree (bronchoconstrictors)

that constrict the bronchiolar diameters when the need for oxygen has diminished, inhibitors to the pulmonary vessels (vasodilators), and secretors to the glands of the bronchial tree (secretomotors). The afferent fibers are sensory to the respiratory epithelium (touch and pain) and to the branches of the bronchial tree (stretch). While efferent nerve tissue innervates smooth muscle cells all the way from the trachea 20 to the terminal bronchioles, the afferent fiber innervations is largely limited to the trachea 20 and larger bronchi. The efferent fibers of sympathetic fibers are inhibitors of the bronchial tree (bronchodilators) that dilate bronchioles of the lung and allows for greater alveolar oxygen exchange, motors to the pulmonary vessels (vasoconstrictors), and inhibitors to the glands of the bronchial tree. The function of afferent fibers of sympathetic fibers is unknown.

Any portion of the autonomic nervous system of a patient that controls, regulates, or affects airways in the lungs may be modulated to reduce narrowing in the airways. In certain embodiments, the activity of the parasympathetic nerves and/or sympathetic nerves in a pulmonary plexus is modulated. In certain other embodiments, the activity of the bronchial branch of the vagus nerve is modulated. Additional nerves that may be modulated include and are not limited to efferent parasympathetic nerves, afferent parasympathetic nerves, c-fibers, vagal a and b fibers, and other individual nerve fibers or tissues (e.g., nerve cells, dendrites, and supporting tissue such as neuroglia). Such nerve tissues may be along the right and/or left main bronchi of the lung root as well as along more distal airways within the lungs. The nerve can be within or outside of the airway wall.

In certain embodiments, modulating nerve activity has a sustained effect on reducing narrowing of an airway in a lung (e.g., by permanently damaging a portion of the parasympathetic nervous system). In certain other embodiments, modulating nerve activity has a transient effect on reducing narrowing of an airway in a lung (e.g., by temporarily blocking nervous system signals).

Preferably, the nerve activity-modulating treatment is targeted to the lungs (i.e., the treatment primarily affects nerve activities that control or regulate the lungs, and does not substantially affects nerve activities that control or regulate other organs). For example, because some of the nerve tissue in the network of nerve trunks 45 coalesces into other nerves (e.g., nerves connected to the esophagus, nerves through the chest and into the abdomen, and the like), specific sites should be selected to minimize, limit, or substantially eliminate unwanted influence on nerve activities that affect organs other than the lungs. In certain embodiments, the nerve activity near the carina is modulated. For example, tissue near the carina may be denervated, which inhibits, limits, or substantially eliminate sensory input that triggers reflex central constriction and/or local constriction caused by c-fibers.

Modulating nerve activity in a portion of the autonomic nervous system of a patient may be performed by attenuating activity in a portion of the parasympathetic nervous system of the patient. Alternatively, modulating nerve activity may be performed by enhancing activity in a portion of sympathetic nervous system of the patient.

Attenuating nerve activity includes, without limitation, hindering, limiting, blocking, and/or interrupting the transmission of signals. For example, the attenuation can include decreasing signal amplitude of nerve signals or weakening the transmission of nerve signals. Decreasing or stopping nervous system input to distal airways can alter airway smooth muscle tone, airway mucus production, airway inflammation, and the like, thereby controlling airflow into and out of the lungs 10. Decreasing or stopping sensory input from the airways and lungs to local effector cells or to the central nervous system can also decrease reflex bronchoconstriction, reflex mucous production, release of inflammatory mediators, and nervous system input to other cells in the lungs or organs in the body that may cause airway wall edema. In some embodiments, the nervous system input can be decreased to correspondingly decrease airway smooth muscle tone. In some embodiments, the airway mucus production can be decreased a sufficient amount to cause a substantial decrease in coughing and/or in airflow resistance. In some embodiments, the airway inflammation can be decreased a sufficient amount to cause a substantial decrease in airflow resistance and ongoing inflammatory injury to the airway wall. Signal attenuation may allow the smooth muscles to relax, prevent, limit, or substantially eliminate mucus production by mucous producing cells, and decrease inflammation.

Attenuating nerve activity in a portion of the parasympathetic nervous system may be performed by damaging the portion of the parasympathetic nervous system (e.g., by applying energy or chemicals). Alternatively, attenuating nerve activity in a portion of the parasympathetic nervous system may be performed by stimulating the portion of the parasympathetic nervous system with electrical impulses to block nervous system signals from traveling past the portion of the parasympathetic nervous system. Attenuating nerve activity in a portion of the parasympathetic nervous system may additionally be performed by non-blocking stimulation of a portion of the parasympathetic system (e.g., vagal A and B fibers) (see, e.g., US 2010/0228318, incorporated herein by reference in its entirety). Attenuating nerve activity in a portion of the parasympathetic nervous system may additionally be performed by preventing the release or production of a neurotransmitter at the prejunctional and/or postjunctional neurons, thereby preventing the neurotransmitters from influencing postjunctional activities.

In certain embodiments, attenuating nerve activity in a portion of the parasympathetic nervous system comprises damaging a nerve trunk extending along a wall of an airway. In some other embodiments, attenuating nerve activity in a portion of the parasympathetic nervous system comprises damaging a bronchial branch of the vagus nerve.

Damaging a portion of the parasympathetic nervous system may be performed using various techniques, such as by applying energy (e.g., from an interventional device) to nerves at a target site (e.g., a nerve trunk extending along a wall of an airway or a bronchial branch of the vagus nerve) either from within the airway or from outside the airway. In certain embodiments, a treatment system (e.g., a catheter) can be navigated through airways, such as the right and left main bronchi of the lung root, as well as more distal airways within the lungs of a patient having a narrowed airway in a lung such as intermediate bronchi, segmental bronchi and subsegmental bronchi. A collapsible ablation assembly can be conveniently passed through airways. An energy emitter assembly of the ablation assembly can treat one or more target sites without treating non-targeted sites. For example, the treatment system can destroy nerve tissue at target sites without destroying to any significant extent, or causing any permanent damage to, non-nerve tissue (e.g., interior airway walls) so that the non-nerve tissue can remain functional after performing treatment. The energy emitter assembly may be cooled to protect non-targeted tissue. Energy that can be used to damage a portion of the parasympathetic nervous system includes without limitation thermal energy, microwave, electrical energy, cryogenic energy, acoustic energy, radio frequency energy, pulsed high voltage energy, mechanical energy (e.g., surgery), ionizing radiation, optical energy (e.g., light energy), and a combination thereof. In certain embodiments, damaging nerves ("denervating") can include damaging all of the nerve tissue of a section of a nerve trunk along an airway to stop substantially all the signals from traveling through the damaged section of the nerve trunk to more distal locations along the bronchial tree or from the bronchial tree more proximally to the central nervous system. Additionally, signals that travel along nerve fibers that go directly from sensory receptors (e.g., cough and irritant receptors) in the airway to nearby effector cells (e.g., postganglionic nerve cells, smooth muscle cells, mucous cells, inflammatory cells, and vascular cells) will also be stopped. If multiple nerve trunks extend along the airway, each nerve trunk can be damaged. As such, the nerve supply along a section of the bronchial tree can be cut off.

In certain embodiments, a nerve activity-modulating treatment comprises modulating nerve activity along an airway ("first airway") of the patient, so that the activity in a nerve that carries signals to or from an obstructed airway that is a higher generation airway of the first airway is modulated. For the purpose of this disclosure, airway branches are numbered in generations starting down from the main stem at generation 0, continuing to the main bronchi at generation 1, and on to the most distal branches at generation 2 and higher. For example, main bronchi 21, 22 (i.e., airway generation 1) of FIG. 1 can be treated (i.e., denervated) to affect distal portions of the bronchial tree 27. In some embodiments, the left and right main bronchi 21, 22 are treated at locations along the left and right lung roots 24 and outside of the left and right lungs 11, 12. Treatment sites can be distal to where vagus nerve branches connect to the trachea and the main bronchi 21, 22 and proximal to the lungs 11, 12. A single treatment session involving two therapy applications can be used to treat most of or the entire bronchial tree 27. Substantially all of the bronchial branches extending into the lungs 11, 12 may be affected to provide a high level of therapeutic effectiveness.

In some embodiments, damaging a portion of the parasympathetic nervous system comprises damaging nerve tissue of a first main bronchus to substantially prevent nervous system signals from traveling to substantially all distal bronchial branches connected to the first main bronchus. In some embodiments, most or all of the bronchial branches distal to the first main bronchus are treated. The damaged nerve tissue, in certain embodiments, is positioned between a trachea and the lung through which the bronchial branches extend. In certain embodiments, a second main bronchus may be further substantially damaged to substantially prevent nervous system signals from traveling to substantially all distal bronchial branches connected to the second main bronchus.

In certain procedures, lesions are formed at the treatment site to attenuate the transmission of signals traveling along the vagus nerves 41, 42 that cause or mediate muscle contractions, mucus production, inflammation, edema, and the like. Lesions can include ablated tissue, scar tissue, openings (e.g., openings of hollow myelin sheaths), or the like. Such lesions can inhibit or prevent nerve tissue regrowth, thereby preventing an unwanted amount of functional recovery for a desired period of time. To inhibit reinnervation, axons, myelin, endoneurium or other structures can be targeted.

Exemplary treatment systems and methods for damaging a portion of the parasympathetic (vagus) nervous system include those described in U.S. Pat. No. 8,088,127, PCT Application Publication Nos. WO 2011/060200, WO 2011/056684, WO 2011/060201, WO 2013/052501, and U.S. Application Publication Nos. 2011/0118725, 2011/0301587, and 2013/0310822. Each of these applications is incorporated herein by reference in its entirety.

For example, in certain embodiments, nerve activity-modulating treatment comprises (i) positioning a treatment device in a first airway of the patient, and (ii) delivering energy from the treatment device into a wall of the first airway to reduce airway obstruction in a second airway that is a higher generation airway than the first airway. The first airway may be an airway between a trachea and a lung, a left or right main bronchus or a bronchus intermedius, or a first generation airway located outside the left and right lungs. In one embodiment, step (ii) may include delivering energy to damage a nerve trunk extending along the first airway, such as a nerve trunk disposed within connective tissue surrounding the wall of the first airway. The treatment device may comprise an energy emitter for delivering energy to the nerve trunk. Step (ii) may further comprise inhibiting damage to airway tissue disposed radially between the treatment device and the nerve trunk, such as by cooling the airway tissue using the treatment device, including absorbing heat from the airway tissue with a cooling element on the treatment device, by actively cooling the airway tissue by circulating a coolant through an expandable member, and by cooling the treatment device.

Figure 2:
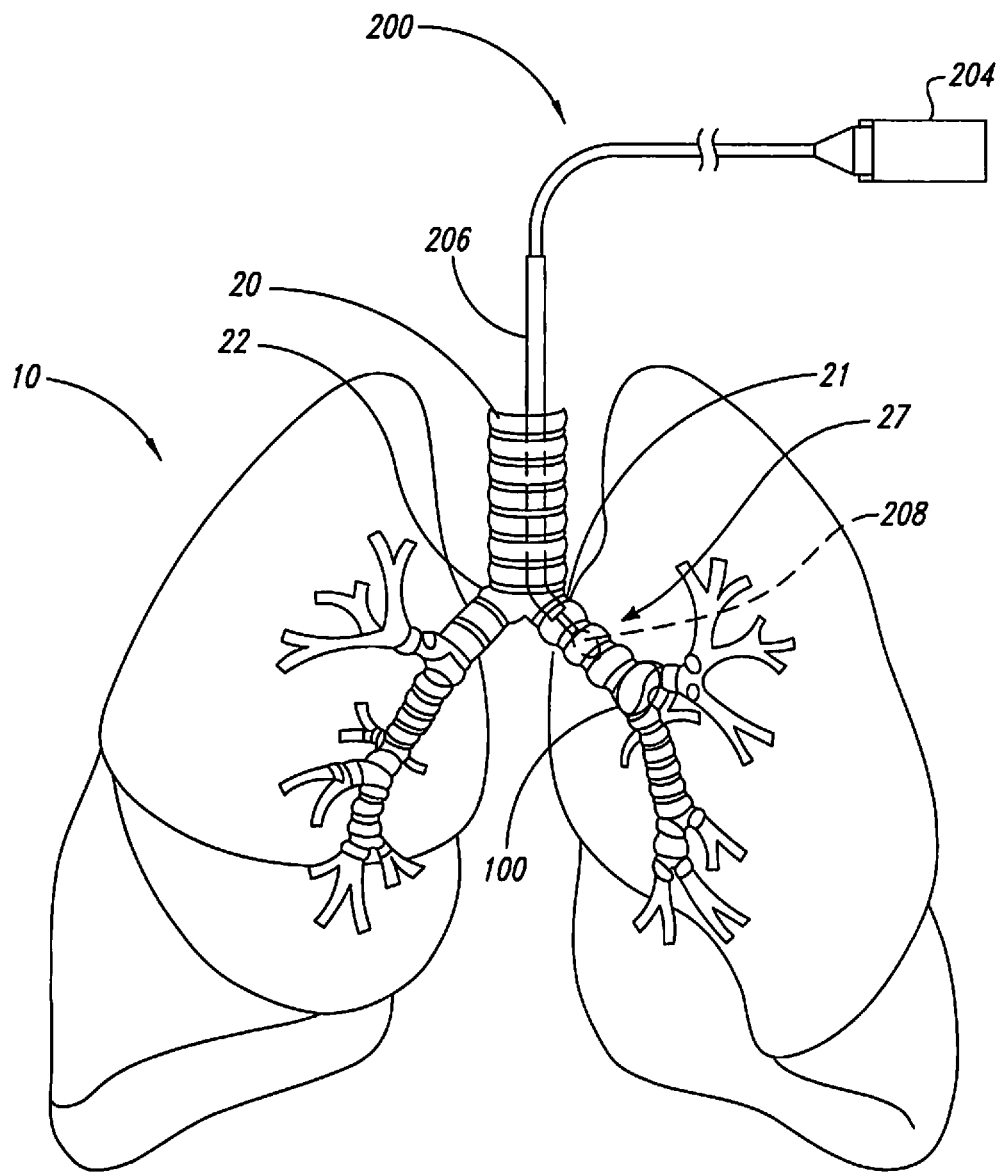
FIG. 2 is an illustration of a delivery device extending from a delivery apparatus positioned in the left main bronchus.

An exemplary treatment device is shown in FIG. 2. FIG. 2 shows a delivery device in the form of a catheter system 204 extending through a delivery apparatus 206. The catheter system 204 can treat airways of the main bronchi 21, 22, as well as airways that are distal to the main bronchi 21, 22. An ablation assembly 208 can be positioned outside the lung which is within the right or left main bronchi, the lobar bronchii, and bronchus intermedius. The intermediate bronchus is the portion of the right main bronchus and the origin of the middle and lower lobar bronchii. The ablation assembly 208 can be positioned in higher generation airways (e.g., airway generations >2) to affect remote distal portions of the bronchial tree 27. The catheter system 204 can be navigated through tortuous airways to perform a wide range of different procedures, such as, for example, denervation of a portion of a lobe, an entire lobe, multiple lobes, or one lung or both lungs. In some embodiments, the lobar bronchi are treated to denervate lung lobes. For example, one or more treatment sites along a lobar bronchus may be targeted to denervate an entire lobe connected to that lobar bronchus. Left lobar bronchi can be treated to affect the left superior lobe and/or the left inferior lobe. Right lobar bronchi can be treated to affect the right superior lobe, the right middle lobe, and/or the right inferior lobe. Lobes can be treated concurrently or sequentially. In some embodiments, a physician can treat one lobe. Based on the effectiveness of the treatment, the physician can concurrently or sequentially treat additional lobe(s). In this manner, different isolated regions of the bronchial tree can be treated.

Each segmental bronchus may be treated by delivering energy to a single treatment site along each segmental bronchus. For example, the catheter system 204 can deliver energy to each segmental bronchus of the right lung. In some procedures, ten applications of energy can treat most of or substantially all of the right lung. In some procedures, most or substantially all of both lungs are treated using less than thirty-six different applications of energy. Depending on the anatomical structure of the bronchial tree, segmental bronchi can often be denervated using one or two applications of energy.

Function of other tissue or anatomical features, such as the mucous glands, cilia, smooth muscle, body vessels (e.g., blood vessels), and the like can be maintained when nerve tissue is ablated. Nerve tissue includes nerve cells, nerve fibers, dendrites, and supporting tissue, such as neuroglia. Nerve cells transmit electrical impulses, and nerve fibers are prolonged axons that conduct the impulses. The electrical impulses are converted to chemical signals to communicate with effector cells or other nerve cells. By way of example, a portion of an airway of the bronchial tree 27 can be denervated to attenuate one or more nervous system signals transmitted by nerve tissue. Denervating can include damaging all of the nerve tissue of a section of a nerve trunk along an airway to stop substantially all the signals from traveling through the damaged section of the nerve trunk to more distal locations along the bronchial tree or from the bronchial tree more proximally to the central nervous system. Additionally, signals that travel along nerve fibers that go directly from sensory receptors (e.g., cough and irritant receptors) in the airway to nearby effector cells (e.g., post-ganglionic nerve cells, smooth muscle cells, mucous cells, inflammatory cells, and vascular cells) will also be stopped. If a plurality of nerve trunks extends along the airway, each nerve trunk can be damaged. As such, the nerve supply along a section of the bronchial tree can be cut off. When the signals are cut off, the distal airway smooth muscle can relax leading to airway dilation, mucous cells decrease mucous production, or inflammatory cells stop producing airway wall swelling and edema. These changes reduce airflow resistance so as to increase gas exchange in the lungs 10, thereby reducing, limiting, or substantially eliminating one or more symptoms, such as breathlessness, wheezing, chest tightness, and the like. Tissue surrounding or adjacent to the targeted nerve tissue may be affected but not permanently damaged. In some embodiments, for example, the bronchial blood vessels along the treated airway can deliver a similar amount of blood to bronchial wall tissues and the pulmonary blood vessels along the treated airway can deliver a similar amount of blood to the alveolar sacs at the distal regions of the bronchial tree 27 before and after treatment. These blood vessels can continue to transport blood to maintain sufficient gas exchange. In some embodiments, airway smooth muscle is not damaged to a significant extent. For example, a relatively small section of smooth muscle in an airway wall which does not appreciably impact respiratory function may be reversibly altered. If energy is used to destroy the nerve tissue outside of the airways, a therapeutically effective amount of energy does not reach a significant portion of the non-targeted smooth muscle tissue.

In some embodiments, one of the left and right main bronchi 21, 22 is treated to treat one side of the bronchial tree 27. The other main bronchus 21, 22 can be treated based on the effectiveness of the first treatment. For example, the left main bronchus 21 can be treated to treat the left lung 11. The right main bronchus 22 can be treated to treat the right lung 12. In some embodiments, a single treatment system can damage the nerve tissue of one of the bronchi 21, 22 and can damage the nerve tissue of the other main bronchus 21, 22 without removing the treatment system from the trachea 20. Nerve tissue positioned along the main bronchi 21, 22 can thus be damaged without removing the treatment system from the trachea 20. In some embodiments, a single procedure can be performed to conveniently treat substantially all, or at least a significant portion (e.g., at least 50%, 70%, 80%, 90% of the bronchial airways), of the patient's bronchial tree. In other procedures, the treatment system can be removed from the patient after treating one of the lungs 11, 12. If needed, the other lung 11, 12 can be treated in a subsequent procedure.

Figure 3:
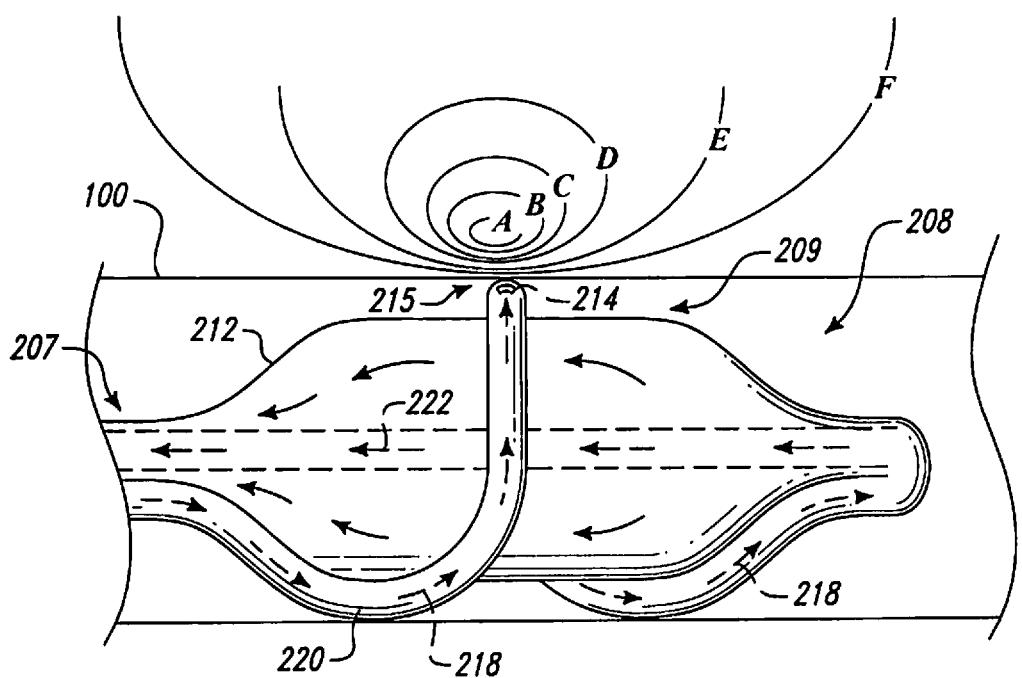
FIG. 3 is a side elevational view of an ablation assembly in an airway.

FIG. 3 shows the effect produced by superficial and deep heating by RF energy and superficial cooling by circulating coolant in the ablation assembly 208. A cooling section 209 of the ablation assembly 208 contains coolant to cool tissue adjacent to a tissue-contacting portion 215 of the energy emitter assembly 220 when energy is outputted. The cooling section 209 can absorb a sufficient amount of thermal energy from the airway wall 100 to limit or prevent damage to the tissue between the energy emitter assembly 220 and the nerve tissue or other targeted tissue.

More specifically, FIG. 3 shows a cross-sectional temperature profile in a section of the airway wall through which the RF energy is delivered to ablate tissue. The terms "ablate" or "ablation," including derivatives thereof, include, without limitation, substantial altering of electrical properties, mechanical properties, chemical properties, or other properties of tissue. As used herein, the term "ablate," including variations thereof, refers, without limitation, to destroying or to permanently damaging, injuring, or traumatizing tissue. For example, ablation may include localized tissue destruction, cell lysis, cell size reduction, necrosis, or combinations thereof. In the context of pulmonary ablation applications, the term "ablation" includes sufficiently altering nerve tissue properties to substantially block transmission of electrical signals through the ablated nerve tissue.

In FIG. 3, arrows 218 represent movement of the coolant through the energy emitter assembly 220. Arrows 222 represent movement of the coolant through a deployable element, illustrated as a distensible and thermally conductive balloon 212. Isothermal curves show the temperatures that are reached at the electrode 214 and at different depths into the airway wall 100 from the electrode-tissue interface when power is applied to the electrode 214 and coolant (e.g., a room temperature saline solution or iced saline) is delivered to the balloon 212. The term "element" in the context of "expandable element" includes a discrete element or a plurality of discrete elements. By way of example, an expandable element can be a single balloon or a plurality of balloons in fluid communication with one another.

By adjusting the rate of power delivery to the electrode 214, the rate at which coolant (e.g., saline solution) is passed into the balloon 212, the temperature of the saline solution, and the size of the balloon 212, and the exact contour and temperature of the individual isotherms can be modified. For example, by selecting the proper temperature and flow rate of saline and the rate of power delivery to the electrode, it is possible to achieve temperatures in which isotherm A=60° C., B=55° C., C=50° C., D=45° C., E=40° C., and F=37° C. Further adjustments make it possible to achieve temperatures where isotherm A=50° C., B=47.5° C., C=45° C., D=42.5° C., E=40° C., and F=37° C. Only those areas contained within the 50° C. isotherm will be heated enough to induce cell death. In some procedures, tissue at a depth of about 2 mm to about 8 mm in the airway wall can be ablated while other non-targeted tissues at a depth less than 2 mm in the airway wall are kept at a temperature below at temperature that would cause cell death. The coolant 218 can absorb energy to cool the tissue-contacting portion 215 of the energy emitter assembly 220 while the balloon 212 holds the energy emitter assembly 220 against the airway 100.

Figure 4:
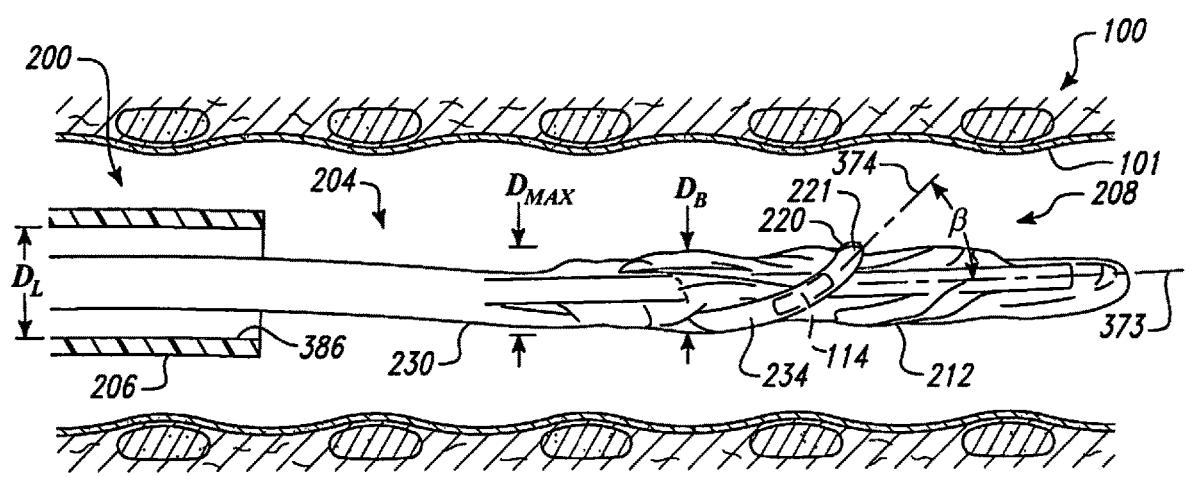
FIG. 4 is a partial cross-sectional view of a treatment system with a delivery device extending out of a delivery apparatus.
Figure 5:
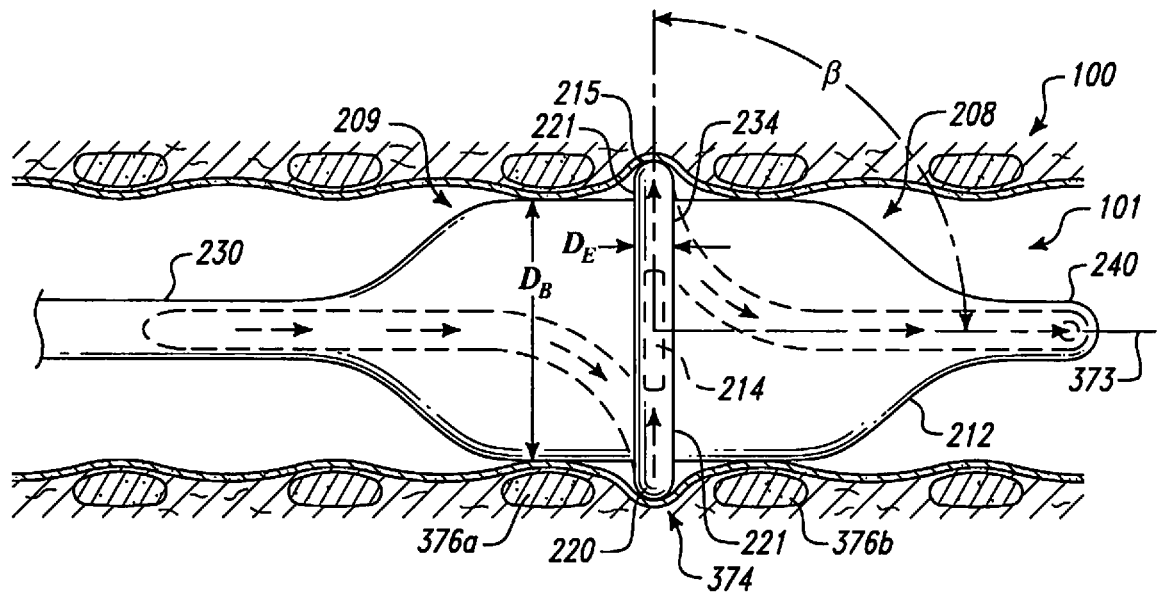
FIG. 5 is a side elevational view of a deployed ablation assembly with fluid flowing through an energy emitter assembly.
Figure 6:
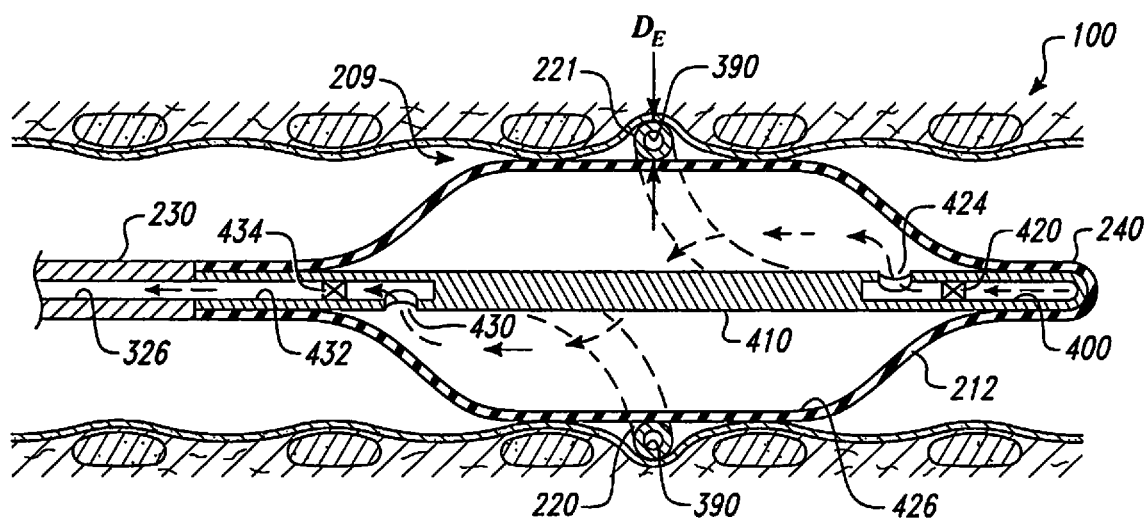
FIG. 6 is a cross-sectional view of the deployed ablation assembly with fluid flowing through an expandable member.

FIGS. 4-6 show one exemplary method of using the treatment system 200. A physician can visually inspect the airway 100 using the delivery apparatus 206 to locate and evaluate the treatment site(s) and non-targeted tissues before, during, and/or after performing a therapy. The delivery apparatus 206 can be a guide tube, a delivery sheath, a bronchoscope, or an endoscope and can include one or more viewing devices, such as optical viewing devices (e.g., cameras), optical trains (e.g., a set of lens), and the like. For example, the delivery apparatus 206 can be a bronchoscope having one or more lights for illumination and optical fibers for transmitting images. The catheter 207 may be adapted to be delivered over a guidewire (not shown) that passes between the balloon 212 and the energy emitter assembly 220. This provides for rapid exchange capabilities.

When the delivery apparatus 206 of FIG. 4 is moved along a body lumen 101 (e.g., airway), the collapsed ablation assembly 208 is held within a working channel 386 of the delivery apparatus 206. The conduit 234 can form a loop 221 such that the electrode 214 is almost parallel to a long axis 373 when the catheter 207 is in a substantially straight configuration. In the illustrated embodiment of FIG. 5, an angle θ is defined between the direction of the long axis 373 of the catheter 207 and a long axis 374 of the electrode 214. The angle β can be in a range of about 0 degrees to about 30 degrees. In some embodiment, the angle β is in a range of about 0 degrees to about 20 degrees. The electrode 214, being curved, can also nest with and partially encircle the elongate shaft 230. In certain embodiments, at least a portion of the elongate shaft 230 is disposed within an arc of the electrode 214 for a further reduced profile. As such, the shaft 230 can be positioned between the ends of the electrode 214. Electrode 214 may have various lengths, depending on the desired length of the lesion to be created in each electrode position. In preferred embodiments, electrode 214 has a length of at least about 2 mm up to about 3 mm. The electrode can have a width (or diameter if cylindrical) no larger than the width of the spaces between the cartilage rings, preferably in some embodiments being 0.1 to about 3 mm.

With continued reference to FIG. 4, the diameter $D_L$ of the working channel 386 can be less than about 8 mm. The diameter $D_B$ of the deflated balloon 212 can be relatively small. For example, a minimum diameter $D_{B\ min}$ can be in a range of about 2 mm to about 3 mm, and a maximum diameter $D_{B\ max}$ in a range of about 5 mm to about 6 mm when the balloon 212 is fully collapsed. If the electrode 214 is collapsible, the diameter $D_{max}$ of the ablation assembly 208 can be less than about 3 mm. In ultra low-profile configurations, the maximum diameter $D_{max}$ can be less than about 2.8 mm.

The balloon 212 can be inflated to move the energy emitter assembly 220 near (e.g., proximate to or in contact with) the airway 100. The angle θ can be increased between 70 degrees and about 110 degrees when the balloon 212 is fully inflated. FIG. 6 shows the ablation assembly 208 deployed, wherein the electrode 214 can be about perpendicular to the long axis 373. There can be play between the energy emitter assembly 220 and the balloon 212 such that the angle β is in a range of about 60 degrees to about 120 degrees in order to accommodate variations of anatomical structures, mis-alignment (e.g., mis-alignment of the catheter shaft 230), or the like. In some embodiments, the electrode 214 moves towards a circumferentially extending orientation as it moves from a delivery orientation to the deployed orientation. The electrode 214 in the deployed orientation extends substantially circumferentially along the wall of the airway 100. In certain embodiments, the electrode 214 will be configured to be positioned entirely within the spaces 374 between cartilage rings 376 along the airway wall when the ablation assembly 208 is in the fully deployed configuration.

FIGS. 5 and 6 show the energy emitter assembly 220 fluidically coupled to both the elongate shaft 230 and the balloon 212. Generally, coolant cools the tissue-contacting portion 215 of the energy emitter assembly 220. The cooling section 209 of the ablation assembly 208 contacts the airway wall 100 so as to cool tissue adjacent to the tissue-contacting portion 215 while energy is outputted by the electrode 214. The cooling section 209 can be formed by the portions of the energy emitting assembly 220 and the balloon 212 that contact the airway wall 100.

As the balloon 212 inflates, the electrode 214 moves (e.g., pivots, rotates, displaces, etc.) from a first orientation of FIG. 4 in which the electrode 214 extends axially along the airway 100 and a second orientation of FIG. 5 in which the entire electrode 214 is disposed in a space 374 between adjacent cartilage rings 376a, 376b. The balloon 212 can both cool the airway 100 and cause the electrode 114 to seat in the space 374.

FIG. 5 shows the energy emitter assembly 220 positioned to locate the electrode 214 in the space 374. In certain embodiments, the electrode 214, in the first orientation, extends a distance with respect to a longitudinal axis 373 (see FIG. 4) can be greater than the distance the electrode 214, in the second orientation, extends with respect to the longitudinal axis 373.

To deploy the energy emitting assembly 208, coolant from the elongate shaft 230 flows through the energy emitter assembly 220 and into the balloon 212. The electrode 214 can output a sufficient amount of energy to ablate a target region. The coolant absorbs thermal energy from electrode 214 and the airway wall 100.

The diameter $D_E$ of the electrode 214 and conduit 234 can be in a range of about 1.5 mm to about 2.5 mm when pressurized with coolant. Such embodiments are well suited to treat tissue outside the lung along the main bronchi. In certain embodiments, the diameter $D_E$ is about 2 mm. In yet other embodiments, the diameter $D_E$ can be in a range of about 0.1 mm to about 3 mm. The diameter $D_E$ of the deflated conduit 234 and electrode 214 can be about 0.1 mm to about 1 mm.

To treat a bronchial tree of a human, the diameter of the inflated balloon 212 can be in a range of about 12 mm to about 18 mm. For enhanced treatment flexibility, the inflated balloon diameter may be in a range of about 7 mm to about 25 mm. Of course, the balloon 212 can be other sizes to treat other organs or tissue of other animals.

The ablation assembly 208 provides differential cooling because the coolant in the energy emitter assembly 220 is at a lower temperature and higher velocity than the coolant in the balloon 212. Coolant, represented by arrows, flows out of the elongate shaft 230 and into the energy emitter assembly 220. The coolant proceeds through the energy emitter assembly 220 and the coolant channel 340 of the electrode 214. The coolant absorbs thermal energy from the electrode 214. The heated coolant flows into the tip 240 and proceeds proximally through a lumen 400, as shown in FIG. 6. The coolant flows through a valve 420 (e.g., a throttle) and passes through a port 424. The valve 420 is disposed along a fluid path connecting the energy emitting assembly 220 and the portion of the balloon 212 defining the cooling section 209. The coolant circulates in a chamber 426 and absorbs heat from the tissue. This helps keep shallow tissue below a temperature that would cause cell death or tissue damage.

The coolant flows through a port 430, a lumen 432, and a throttle 434. The throttles 420, 434 can cooperate to maintain a desired pressure. The throttle 420 is configured to maintain a first flow rate of the coolant through the energy emitting assembly 220 and a second flow rate of the coolant through the cooling section 209. The first flow rate can be significantly different from the second flow rate.

The conduit 234 can assume a preset shape when pressurized. The valves 420, 434 can cooperate to maintain the desired pressure within the balloon 212 within a range of about 5 psig to about 15 psig. Such pressures are well suited to help push the electrode 214 between cartilaginous rings. Other pressures can be selected based on the treatment to be performed. The valves 420, 434 can be throttle valves, butterfly valves, check valves, duck bill valves, one-way valves, or other suitable valves.

When RF energy is transmitted to the electrode 214, the electrode 214 outputs RF energy that travels through tissue. The RF energy can heat tissue (e.g., superficial and deep tissue) of the airway wall while the coolant cools the tissue (e.g., superficial tissues). The net effect of this superficial and deep heating by RF energy and superficial cooling by the circulating coolant is the concentration of heat in the outer layers of the airway wall. The temperature of the connective tissue can be higher than the temperatures of the epithelium, stroma, and/or smooth muscle. By example, the temperature of the connective tissue can be sufficiently high to cause damage to the nerve trunk tissue or other deep tissue while other non-targeted tissues of the airway are kept at a lower temperature to prevent or limit damage to the non-targeted tissues.

Heat can be concentrated in one or more of the internal layers (e.g., the stroma) of the airway wall or in the inner lining (e.g., the epithelium) of the airway wall. Furthermore, one or more of the vessels of the bronchial artery branches may be within the lesion. The heat generated using the electrode 214 can be controlled such that blood flowing through the bronchial artery branches protects those branches from thermal injury while nerve trunk tissue is damaged, even if the nerve tissue is next to the artery branches. The catheter 207 can produce relatively small regions of cell death. For example, a 2 mm to 3 mm section of tissue in the middle of the airway wall 100 or along the outer surface of the airway wall 100 can be destroyed. By the appropriate application of power and the appropriate cooling, lesions can be created at any desired depth.

A circumferential lesion can be formed around all or most of the circumference of the airway wall 100 by ablating tissue while slowly rotating the ablation assembly 208 or by positioning the ablation assembly 208 in a series of rotational positions at each of which energy is delivered for a desired time period. Some procedures form adjacent lesions that become contiguous and form a circumferential band all the way around the airway wall 100. In some embodiments, the entire loop 221 (FIG. 5) can be an electrode. The loop 221 can be coated with a conductive material and can carry the electrode. A single procedure can produce a circumferential lesion. After forming the lesion, coolant flowing into the balloon 212 can be stopped. The balloon 212 is deflated causing the energy emitter assembly 220 to recoil away from the airway wall 100. The catheter 207 may be repositioned to treat other locations or removed from the subject entirely.

Additional techniques for damaging, either temporarily or permanently, a portion of the parasympathetic nervous system include vagotomy (cutting of the vagus nerve) and bronchial thermoplasty that ablates the airway wall in a multitude of bronchial branches within the lung thereby eliminating smooth muscle and damaging nerves in the airway walls of the lung.

In certain embodiments, a portion of the parasympathetic nervous system may be damaged or can have their function disrupted by delivering one or more chemicals or substances (e.g., radioactive seeds, radioactive materials, etc.) to or near a portion of the parasympathetic nervous system. Exemplary chemicals useful in damaging or disrupting nerves include hypertonic solutions, hypotonic solutions, phenols, alcohols, nerve blocking agents such as lidocaine or tetricaine, neurotoxins such as tetanus toxoid, botulinum toxin, or ricin.

In certain embodiments, attenuating nerve activity in a portion of the parasympathetic nervous system may be performed by stimulating the portion of the parasympathetic nervous system with electrical impulses to block nervous system signals from traveling past the portion of the parasympathetic nervous system. Additional methods include cooling the nerve or mechanically compressing the nerve axons within the nerves, both of which may be achieved with an implant to temporarily decrease nerve functions. Exemplary devices and methods are described in U.S. application Ser. No. 12/372,607, filed Feb. 17, 2009, and issued as U.S. Pat. No. 8,483,831, which is incorporated herein by reference.

Different attributes of airways can be evaluated to determine the effect of a nerve activity-modulating treatment and/or drug administration on the airways. Such airway attributes include, without limitation, physical properties of airways (e.g., airway compliance, contractile properties, etc.), airway resistance, dimensions of airway lumens (e.g., shapes of airways, diameters of airways, etc.), responsiveness of airways (e.g., responsiveness to stimulation), muscle characteristics (e.g., muscle tone, muscle tension, etc.), inflammatory cells, inflammatory cytokines, or the like.

In certain embodiments, modulating nerve activity to reduce narrowing of an airway in a lung of a patient may be performed by enhancing activity in a portion of sympathetic nervous system of the patient. Exemplary devices and methods for stimulating sympathetic nervous system include selective electrical nerve stimulation of the sympathetic nerves or electrical simulation using signals or pulse trains that selectively activate the sympathetic nerves.

"Subsequently administering a drug" to a patient according to the methods of the present disclosure refers to administering a drug to a patient after the nerve activity-modulating treatment. In certain embodiments, the patient has received administration of the drug before the nerve activity-modulating treatment, but received administration of the drug again after the nerve activity-modulating treatment. In certain other embodiments, the patient has not received any administration of the drug before the nerve activity-modulating treatment, and the drug administration after the nerve activity-modulating treatment is the first time that the drug is administered to the patient.

In certain embodiments, the nerve activity-modulating treatment has sustained effects. Following such a treatment (e.g., sustained disruption of the parasympathetic nervous system as induced by vagus nerve disruption), drug administration can be performed at any time after therapy and will lead to enhanced regional delivery of the lungs to the more obstructed portion of the trachea-bronchial tree. In certain other embodiments, the nerve activity-modulating treatment has transient effects. During and following such a treatment (e.g., transient disruption of the parasympathetic nervous system as induced by nerve blocking signals from an implanted or externally applied stimulator/signal generator), drug administration is typically performed during the application of the nerve blocking signal, immediately or after a short period of time (e.g., within 1, 2, 3, 4, 5, 6, 7, 8, 9, or 10 minutes) following the completion of the blocking signal while the transient effect of the nerve activity-modulating treatment has not substantially diminished (e.g., while more than 50% of the effect of the nerve activity-modulating treatment at the end of the treatment is still retained).

Various drugs for treating pulmonary diseases may be administered to a patient after the patient is subject to a nerve activity-modulating treatment. In certain embodiments, such drugs are effective in treating an obstructive lung disease. In certain other embodiments, the drugs may be for treating pulmonary diseases other than obstructive lung diseases. Exemplary drugs useful in the methods disclosed herein include those for treating asthma, acute bronchitis, COPD (including chronic bronchitis and emphysema), cystic fibrosis, tuberculosis, non-tuberculous mycobacterial infections, sardoidosis, Churg-Strauss syndrome, allergic bronchopulmonary aspergillosis, bronchiectasis, influenza, lung cancer, pneumonia, pulmonary edema, pulmonary emboli, pulmonary fibrosis, pulmonary hypertension, sarcoidosis, asbestosis, aspergilloma, aspergillosis, atelectasis, bronchiectasis, pleural effusion, pneumoconiosis, pneumothorax, pulmonary actinomycosis, pulmonary alveolar proteinosis, pulmonary anthrax, pulmonary arteriovenous malformation, pulmonary nocariosis, pulmonary tuberculosis, pulmonary veno-occlusive disease, and rheumatoid lung disease.

In certain embodiments, the drugs are inhaled drugs. Exemplary inhaled drugs include and are not limited to bronchodilators, inhaled glucocorticoids (such as budesonide), inhaled steroids, inhaled anti-inflammatories, inhaled antibiotics (such as tobramycin and cholestine), mucolytics (such as n-acetyl cysteine (Mucomyst)), DNAse (dornase alfa), saline, oxygen, cromolyn, nedocromil, inhaled corticosteroids, expectorants (such as guaifenesin), and methylxanthines. Bronchodilators include anticholinergics (such as ipratropium and tiotropium) and beta agonists (such as albuterol, levalbuterol, salmetemol, formoterol, and arformoterol).

As described above, improvements in regional airflow may lead to concomitant improvements in matched regional blood flow, and consequently improve delivery of drugs to the lungs through the blood stream. Thus, in certain embodiments, the drugs are non-inhaled drugs. Such drugs are varied, including broad classes of oral and injected medications that might be more effective with improve delivery to areas of the lung. Exemplary non-inhaled drugs include but are not limited to theophylline, prednisone, methylprednisilone, epinephrine, and antibiotics such as azithromycin, amoxicillin, ceftriaxone, pipericillin, leukotriene modifiers.

Additional exemplary drugs that may be delivered to a lung of a patient after a nerve activity-modulating treatment include but are not limited to aminophylline, ampicillin, beclomethasone dipropionate, bupropion hydrochloride, cefaclor, cefadroxil, cefixime, cefprozil, cefuroxime axetil, cephalexin, ciclesonide, ciprofloxacin hydrochloride, clarithromycin, clindamycin, cloxacillin, erythromycin, ethambutol, fenoterol hydrobromide, fluconazole, flunisolide, fluticasone furoate, fluticasone propionate, indacaterol maleate, isoniazid, itraconazole, ketoconazole, ketotifen, levofloxacin, minocycline, mometasone furoate, montelukast sodium, moxifloxacin, nicotine, nystatin, ofloxacin, omalizumab, orciprenaline, oseltamivir, oxtriphylline, penicillin, pivampicillin, pyrazinamide, rifampin, roflumilast, cromoglycate, telithromycin, terbutaline sulfate, triamcinolone acetonide, varenicline, zafirlukast, and zanamivir.

The drugs may be administered to a patient via various routes. Inhaled drugs are typically administered via inhalation. Non-inhaled drugs may be administered enterally, such as orally, by gastric feeding tube, duodenal feeding tube, or gastrostomy, or rectally in suppository. Alternatively, such drugs may be administered parenterally, such as intravenously, intra-arterially, intraosseous infusion, intra-muscularly, intracerebrally, intracerebroventricularly, subcutaneously, or the like.

The drugs are administered to a patient in need at a therapeutically effective dose. A "therapeutically effective dose" of a drug refers to the amount of the drug sufficient to result in reducing the severity of, eliminating, or delaying the onset or reoccurrence of one or more symptoms of a disease or disorder at issue in a statistically significant manner. Such a dose may be determined or adjusted depending on various factors including the specific drug, the route of administration, the patient's condition, that is, stage of the disease, severity of symptoms caused by the disease, general health status, as well as age, gender, and weight, and other factors apparent to a person skilled in the medical art. Similarly, the dose of the drug for treating a disease or disorder may be determined according to parameters understood by a person skilled in the medical art. Optimal doses may generally be determined using experimental models and/or clinical trials. Design and execution of pre-clinical and clinical studies for a therapeutic agent (including when administered for prophylactic benefit) described herein are well within the skill of a person skilled in the relevant art.

In certain embodiments, the amount of a drug administered to a patient after a nerve activity-modulating treatment may be less than the amount required in a patient without the nerve activity-modulating treatment. The nerve activity-modulating treatment improves drug delivery to a lung of the patient and thus efficacy of the drug. Reducing the amount required for the drug to be effective may also reduce the potential side effects associated with an excessive amount of the drug in certain regions of the lung (e.g., regions of a lung that were minimally obstructed prior to the nerve activity-modulating treatment).

In a second aspect, the present disclosure provides a method for improving drug efficacy in a patient having an obstructive lung disease that comprises administering a drug to a patient who has undergone, prior to the administration of the drug, a procedure that modulates nerve activity in the autonomic nervous system of the patient to reduce airway obstruction in at least one obstructed airway in a lung of the patient, wherein a post-treatment efficacy of the drug following the procedure is improved relative to a reference efficacy of the drug.

This second aspect of the present disclosure is identical to the first aspect of the present disclosure except that the method according to the second aspect comprises administering a drug to a patient who has undergone a nerve activity-modulating treatment, while the method according to the first aspect comprises both steps of a nerve activity-modulating treatment and administration of a drug. The description of the first aspect of the present disclosure (e.g., the description of the drugs and their administration, nerve activity-modulating treatments, a reference efficacy of a drug) is applicable to this second aspect of the present disclosure unless otherwise indicated.

In the second aspect, a "post-treatment efficacy" of a drug following a nerve activity-modulating treatment refers to an improvement in a symptom or a parameter associated with a symptom of a patient who has undergone a nerve activity-modulating treatment relative to a baseline of the symptom or the parameter associated with the symptom before the patient has been subjected to either the nerve activity-modulating treatment or the administration of the drug.

In a third aspect, the present disclosure provides a method for treating a patient having an obstructive lung disease, comprising: (a) modulating nerve activity in the autonomic nervous system of the patient to reduce obstruction in a distal airway in the lung of the patient, and (b) subsequently administering a drug while the obstruction is reduced in the distal airway.

The description of the first aspect of the present disclosure (e.g., the description of the drugs and nerve activity-modulating treatments) is applicable to this third aspect of the present disclosure unless otherwise indicated.

As understood by a person skilled in the medical art, the terms, "treat" and "treatment," refer to medical management of a disease, disorder, or condition of a subject (i.e., patient) (see, e.g., Stedman's Medical Dictionary). "Treating a patient having an obstructive lung disease," as used herein, refers to treating an obstructive lung disease (e.g., COPD) in a patient and/or another disorder (e.g., lung cancer) that a patient having an obstructive lung disease may also have, such as reducing the number of symptoms of a disease at issue (e.g., an obstructive lung disease), decreasing the severity of one or more symptoms of the disease, or delaying the progression of the disease.

In certain embodiments, step (a) is performed without causing permanent damage to non-nerve tissue.

Step (a) may comprise attenuating nerve activity in a portion of the parasympathetic nervous system of the patient. Alternatively, step (a) may comprise stimulating nerve activity in a portion of sympathetic nervous system of the patient.

In some embodiments, step (a) comprises modulating nerve activity along an airway ("first airway") of the patient, so that the activity in a nerve that carries signals to or from an obstructed airway that is a higher generation airway of the first airway is modulated.

In some embodiments, step (a) comprises modulating nerve activity of a pulmonary plexus or modulating nerve activity of a bronchial branch of the vagus nerve.

In certain embodiments, step (a) comprises damaging a portion of the parasympathetic nervous system, such as applying energy to the portion of the parasympathetic nervous system. The portion of the parasympathetic nervous system to which energy is applied may be a nerve trunk extending along a wall of an airway or a bronchial branch of the vagus nerve. The energy may be applied using an interventional device, either from within the airway or from outside the airway. The energy may be thermal energy, microwave, electrical energy, cryogenic energy, acoustic energy, radio frequency energy, pulsed high voltage energy, mechanical energy, ionizing radiation, and/or optical energy.

Preferably, applying energy to the portion of parasympathetic nervous system does not cause permanent damage to any interior airway walls of the patient. This may be accomplished by protecting an interior airway wall of the patient from permanent damage while applying the energy.

In certain embodiments, step (a) comprises stimulating the portion of the parasympathetic nervous system with electrical impulses to block nervous system signals from traveling past the portion of the parasympathetic nervous system.

The drugs that may be applied to a patient may be those described in connection with the methods according to the first aspect of the present disclosure. For example, the drug may be an inhaled drug, such as a bronchodilator (e.g., an anticholinergic or a beta antagonist), and a steroid, an anti-inflammatory, or an antibiotic. Alternatively, the drug may be a non-inhaled drug (e.g., an injected or intervenous drug), including theophylline, prednisone, methylprednisilone, epinephrine, or an antibiotic.

The obstruction in one or more airways in a patient having an obstructive lung disease may result from smooth muscle contraction, thickening of airway wall, mucous accumulation, or a combination thereof.

In certain embodiments, the patient to be treated suffers from chronic obstructive pulmonary disease (COPD), asthma, or cystic fibrosis.

In some embodiments, steps (a) and (b) have a treatment efficacy greater than a reference efficacy of the drug. The terms "treatment efficacy of steps (a) and (b)" and "reference efficacy of a drug" are the same as those terms described in connection with the methods according to the first aspect of the present disclosure. In one embodiment, the reference efficacy of a drug is the efficacy of the drug in the patient prior to step (a).

According to this third aspect of the present disclosure, step (b) is to administer a drug subsequent to a nerve activity-modulating treatment while the obstruction remains reduced in the distal airway by the nerve activity-modulating treatment. For example, if the nerve activity-modulating treatment (e.g., vagal nerve denervation) has a permanent effect on reducing obstructions in a distal airway, the drug may be administered at any time after the nerve activity-modulating treatment. However, if the nerve activity-modulating treatment (e.g., transient disruption of the parasympathetic nervous system induced by nerve blocking signals from an implanted or externally applied stimulator/signal generator) has a transient effect on reducing obstructions in a distal airway, drug administration is performed during, immediately, or after a short period of time while the obstruction in the distal airway remains reduced.

In a fourth aspect, the present disclosure provides a method for treating a patient having an obstructive lung disease that comprises administering a drug to a patient, wherein the patient has undergone a procedure that modulates nerve activity in the autonomic nervous system of the patient to reduce airway obstruction in at least one obstructed airway in a lung of the patient, wherein the drug is administered while the obstruction is reduced in the at least one obstructed airway.

This fourth aspect of the present disclosure is identical to the third aspect of the present disclosure except that the method according to the fourth aspect comprises administering a drug to a patient who has undergone a nerve activity-modulating treatment, while the method according to the third aspect comprises both steps of a nerve activity-modulating treatment and administration of a drug. The description of the third aspect of the present disclosure (e.g., the description of the drugs and their administration and nerve activity-modulating treatments) is applicable to this fourth aspect of the present disclosure unless otherwise indicated.

In certain embodiments according to the fourth aspect of the present disclosure, a post-treatment efficacy of the drug following a nerve activity-modulating treatment is improved relative to a reference efficacy of the drug. In such embodiments, a "post-treatment efficacy" of a drug following a nerve activity-modulating treatment refers to an improvement in a symptom or a parameter associated with a symptom of a patient who has undergone a nerve activity-modulating treatment relative to a baseline of the symptom or the parameter associated with the symptom before the patient has been subjected to either the nerve activity-modulating treatment or the administration of the drug.

In a fifth aspect, the present disclosure provides a method for treating an obstructive lung disease that comprises administering an inhaled drug to a patient of obstructive pulmonary disease, wherein the patient has previously undergone a procedure comprising: (i) positioning a treatment device in a first airway of the patient, and (ii) delivering energy from the treatment device into a wall of the first airway to reduce airway obstruction in a second airway that is a higher generation airway than the first airway.

"Treating an obstructive lung disease," as used herein, refers to reducing the number of symptoms of an obstructive lung disease, decreasing the severity of one or more symptoms of the disease, or delaying the progression of the disease.

Obstructive lung disease is defined above in connection with the description of the methods according to the first aspect of the present disclosure. Exemplary obstructive lung diseases include COPD, asthma, bronchiectasis, and cystic fibrosis. Symptoms of such diseases and methods for monitoring or measuring such symptoms are known in the art, including those described in connection with the description of the methods according to the first aspect of the present disclosure.

Any inhaled drugs effective in treating obstructive pulmonary disease may be used in the methods disclosed herein. Exemplary inhaled drugs include and are not limited to bronchodilators, inhaled glucocorticoids (such as budesonide), inhaled steroids, inhaled anti-inflammatories, inhaled antibiotics (such as tobramycin and cholestine), mucolytics (such as n-acetyl cysteine (Mucomyst)), DNAse (dornase alfa), saline, oxygen, cromolyn, nedocromil, inhaled corticosteroids, expectorants (such as guaifenesin), and methylxanthines. Bronchodilators include anticholinergics (such as ipratropium and tiotropium) and beta agonists (such as albuterol, levalbuterol, salmetemol, formoterol, and arformoterol). The inhaled drugs are administered to a patient via inhalation.

The patients that may be treated by the methods according to the fifth aspect of the present disclosure suffer from an obstructive lung disease and have undergone a procedure that comprise (i) positioning a treatment device in a first airway of the patient, and (ii) delivering energy from the treatment device into a wall of the first airway to reduce airway obstruction in a second airway that is a higher generation airway than the first airway.

The first airway may be an airway between a trachea and a lung, a left or right main bronchus or a bronchus intermedius, or a first generation airway located outside the left and right lungs. In one embodiment, step (ii) may include delivering energy to damage a nerve trunk extending along the first airway, such as a nerve trunk disposed within connective tissue surrounding the wall of the first airway. The treatment device may comprise an energy emitter for delivering energy to the nerve trunk. Step (ii) may further comprise inhibiting damage to airway tissue disposed radially between the treatment device and the nerve trunk, such as by cooling the airway tissue using the treatment device, including absorbing heat from the airway tissue with a cooling element on the treatment device, by actively cooling the airway tissue by circulating a coolant through an expandable member, and by cooling the treatment device.

Exemplary treatment devices useful in the procedure that a patient is subjected to prior to administration of a drug include those described in U.S. Pat. No. 8,088,127, PCT Application Publication Nos. WO 2011/060200, WO 2011/056684, and WO 2011/060201, U.S. Application Publication Nos. 2011/0118725 and 2011/0301587, and U.S. Provisional Application Nos. 61/543,759 and 61/649,154. Each of these applications is incorporated herein by reference in its entirety. Certain exemplary treatment devices and their uses are also shown in FIGS. 2-6 and described in connection with the methods according to the first aspect of the present disclosure.

The obstruction in one or more airways in a patient having an obstructive lung disease may result from smooth muscle contraction, thickening of airway wall, mucous accumulation, or a combination thereof.

In some embodiments, a post-treatment efficacy of a drug following the procedure that the patient has undergone is improved relative to a reference efficacy of the drug. steps (a) and (b) have a treatment efficacy greater than a reference efficacy of the drug. A "post-treatment efficacy" of a drug following a procedure comprising steps (i) and (ii) as described above refers to an improvement in a symptom or a parameter associated with a symptom of a patient who has undergone a procedure comprising steps (i) and (ii) relative to a baseline of the symptom or the parameter associated with the symptom before the patient has been subjected to either the procedure or the administration of the drug. A "reference efficacy" of a drug, as used herein, is the same as this term is used in connection with the description of the first aspect of the present disclosure.

In a sixth aspect, the present disclosure provides a method for treating an obstructive lung disease that comprises (a) (i) positioning a treatment device in a first airway of a patient suffering from an obstructive lung disease, and (ii) delivering energy from the treatment device into a wall of the first airway to reduce airway obstruction in a second airway that is a higher generation airway than the first airway, and (b) subsequently administering an inhaled drug to the patient.

This sixth aspect of the present disclosure is identical to the fifth aspect of the present disclosure except that the method according to the fifth aspect comprises administering a drug to a patient who has undergone a procedure comprising steps (i) and (ii), while the method according to the sixth aspect comprises both a procedure comprising steps (a) and (b) and administration of a drug. The description of the fifth aspect of the present disclosure (e.g., the description of the drugs and their administration and procedures comprising steps (i) and (ii)) is applicable to this sixth aspect of the present disclosure unless otherwise indicated.

In some embodiments, steps (a) and (b) have a treatment efficacy greater than a reference efficacy of the drug. The terms "treatment efficacy of steps (a) and (b)" refers to an improvement in a symptom or a parameter associated with a symptom of a patient resulting from steps (a) and (b) relative to a baseline of the symptom or the parameter associated with the symptom before the patient has been subjected to either step (a) or step (b). A "reference efficacy" of a drug, as used herein, is the same as this term is used in connection with the description of the first aspect of the present disclosure.

In a seventh aspect, the present disclosure provides a method for treating a patient having an obstructive lung disease or bronchial constriction in an airway or a lung, the method including: (a) modulating or attenuating nerve activity in the autonomic nervous system of the patient to reduce obstruction in a distal airway in the lung of the patient; and (b) subsequently or simultaneously administering a drug or combination of drugs that inhibit(s) or prevent(s) the production and/or the release of acetylcholine from parasympathetic nerves at the neuromuscular junction and/or selectively block(s) the binding of acetylcholine to its receptor in nerve cells (e.g. anticholinergics or antimuscarinics).

In this aspect, step (a) can be performed as described in any of the previous aspects described above. In step (b), drugs for selectively blocking the binding of acetylcholine to its receptor in nerve cells can include, for example, anticholinergics (such as ipratropium and tiotropium). Drugs that inhibit the production and/or release of acetylcholine from the prejunctional and/or postjunctional neurons can include, for example, botulinum toxin, which acts to weaken skeletal and smooth muscle by preventing or inhibiting the docking of the acetylcholine vesicle on the inner surface of the presynaptic membrane of the neuron, thus causing chemical denervation and paresis of skeletal or smooth muscle. Additionally, organic mercurial compounds, such as methylmercury, have a high affinity for sulfhydryl groups, which causes dysfunction of the enzyme choline acetyltransferase. This inhibition may lead to acetylcholine deficiency.

In an eighth aspect, the present disclosure provides a method for treating a patient having an obstructive lung disease or bronchial constriction in an airway or a lung, the method including: inhibiting or preventing the binding of acetylcholine with receptors at a neuromuscular junction between a nerve fiber and a muscle cell in a wall of a first airway by inhibiting the release of acetylcholine from the nerve fiber. Inhibiting the release of acetylcholine can comprise injuring, either permanently or temporarily, the nerve fiber proximally of the neuromuscular junction, such as, for example, by any of the methods or devices as previously described, such as, for example ablation. The ablation can be accomplished via delivery of thermal energy, cryogenic energy (e.g., cooling energy), electrical energy, acoustic energy (e.g., ultrasonic energy), radio frequency energy, pulsed high voltage energy, mechanical energy, ionizing radiation, optical energy (e.g., light energy), or combinations thereof, and/or other types of energy suitable for treating tissue, from a device positioned in the airway to the targeted nerve fiber, for example, and as described above.

Additionally or alternatively to injuring the nerve fiber, inhibiting the release of acetylcholine can comprise administration of a drug that inhibits or prevents the production and/or the release of acetylcholine from parasympathetic nerves at the neuromuscular junction, such as, for example, botulinum toxin, and/or organic mercurial compounds, such as methylmercury.

In this embodiment, the corresponding receptors can be open to binding with acetylcholine or blocked to binding via the administration of an anticholinergic agent, for example. In one particular aspect, the method further includes binding an agent, such as by delivery of an anticholinergic agent, to second receptors at a second neuromuscular junction in a wall of a second airway to inhibit or prevent acetylcholine from binding to second receptors. The second airway can be of a higher generation airway than the first airway. In yet another aspect, the method can further include inhibiting the release of acetylcholine by interrupting the nerve fiber, such as by ablation, along a third airway, such as the left and/or right main bronchi, the first airway being a higher generation than the third airway.

In particular, a method of treating bronchial constriction in a lung comprises inhibiting the activation of muscarinic receptors in a postjunctional muscle cell of an airway by inhibiting the release of acetylcholine from a prejunctional and/or postjunctional neuron. Inhibiting the release of acetylcholine comprises injuring, either permanently or temporarily, the neuron, such as by ablating the nerve fiber. Ablation can be accomplished, for example, by using energy delivered from a treatment device, such as the ablation assembly described supra. Additionally or alternatively, inhibiting the release of acetylcholine comprises treating the prejunctional and/or postjuntional neuron with a compound, such as botulinum toxin, that prevents the release of acetylcholine from presynaptic vesicles of the neuron. The muscarinic receptors in this example, can be, for example, M3 receptors located on smooth muscle cells, mucosal glands, and/or vascular endothelium in the wall of an airway.

The method can further include the step of inhibiting the activation of muscarinic receptors in a second postjunctional muscle cell of a second airway, such as a higher generation airway than the first airway, by inhibiting acetylcholine released from a second prejunctional and/or postjuntional neuron from binding to the muscarinic receptors in the second postjunctional muscle cell of the second airway. Inhibiting the release of acetylcholine from the first neuron reduces bronchial constriction by a first amount, and inhibiting acetylcholine from binding to the muscarinic receptors in the second postjunctional muscle cell of the second airway reduces bronchial constriction by a second amount substantially greater than the first amount. Inhibiting the activation of muscarinic receptors can be accomplished, for example, by treatment with an anticholinergic compound. The method can further include the step of inhibiting the release of acetylcholine in a third airway, with the second airway being a higher generation than the third airway.

In this aspect, the method can further include the optional subsequent administration of any of a variety drugs as disclosed in previous embodiments.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method for improving drug efficacy in a patient having an obstructive lung disease, comprising:
administering a therapeutically effective dose of an inhaled anticholinergic drug to the patient, wherein the inhaled anticholinergic drug has a reference efficacy when given as an initial bronchodilator, and a second reference efficacy when given as a second bronchodilator, wherein the patient has undergone, prior to the administration of the inhaled anticholinergic drug, a denervation procedure that includes injuring, either temporarily or permanently, a nerve trunk extending along a wall of an airway or a bronchial branch of the vagus nerve to modulate nerve activity in the autonomic nervous system of the patient by preventing acetylcholine from influencing postjunctional activities to reduce airway obstruction in at least one obstructed airway in a lung of the patient, and wherein a post-treatment efficacy of the inhaled anticholinergic drug following said denervation procedure is greater than the second reference efficacy of the inhaled anticholinergic drug when given as a second bronchodilator.

2. A method for treating a patient having an obstructive lung disease, comprising:
   (a) performing a denervation procedure to modulate nerve activity in an autonomic nervous system of the patient by preventing acetylcholine from influencing postjunctional activities to reduce obstruction in a distal airway in a lung of the patient, wherein the denervation procedure includes injuring, either temporarily or permanently, a nerve trunk extending along a wall of an airway or a bronchial branch of the vagus nerve; and
   (b) subsequently administering a therapeutically effective dose of an inhaled anticholinergic drug while the obstruction is reduced in the distal airway such that the inhaled anticholinergic drug is delivered to the distal airway,
   wherein steps (a) and (b) have a treatment efficacy greater than a reference efficacy of the inhaled anticholinergic drug, wherein the reference efficacy of the inhaled anticholinergic drug is defined as an efficacy of the inhaled anticholinergic drug after the inhaled anticholinergic drug has been administered as a second bronchodilator after administration of a first bronchodilator.

3. The method of claim 2, wherein step (a) is performed without causing permanent damage to non-nerve tissue.

4. The method of claim 2, wherein step (a) comprises attenuating nerve activity in a portion of a parasympathetic nervous system of the patient.

5. The method of claim 2, wherein step (a) also comprises stimulating nerve activity in a portion of a sympathetic nervous system of the patient.

6. The method of claim 2, wherein step (a) comprises modulating nerve activity along a first airway of the patient, the at least one obstructed airway is a higher generation airway of the first airway, and the modulating nerve activity includes modulating activity in a nerve which carries signals to or from the higher generation airway.

7. The method of claim 2, wherein step (a) comprises modulating nerve activity of a pulmonary plexus.

8. The method of claim 2, wherein step (a) comprises modulating nerve activity of a bronchial branch of the vagus nerve.

9. The method of claim 2, wherein step (a) comprises damaging a bronchial branch of the vagus nerve.

10. The method of claim 2, wherein step (a) also comprises stimulating the portion of the parasympathetic nervous system with electrical impulses to block nervous system signals from traveling past the portion of the parasympathetic nervous system.

11. The method of claim 2, wherein the at least one obstructed airway results from smooth muscle contraction, thickening of airway wall, mucous accumulation, or a combination thereof.

12. The method of claim 2, wherein the patient suffers from chronic obstructive pulmonary disease (COPD).

13. The method of claim 2, wherein the patient suffers from asthma.

14. The method of claim 2, wherein the patient suffers from cystic fibrosis.

15. The method of claim 2, further comprising administering the inhaled anticholinergic drug to the patient prior to step (a), wherein steps (a) and (b) have a treatment efficacy greater than an efficacy of the inhaled anticholinergic drug delivered prior to step (a).

16. The method of claim 2, wherein the denervation procedure prevents the acetylcholine from influencing postjunctional activities by inhibiting release and/or production of acetylcholine.

17. The method of claim 2, wherein step (a) comprises damaging a portion of the parasympathetic nervous system.

18. The method of claim 17, wherein damaging the portion of the parasympathetic nervous system comprises applying energy to the portion of the parasympathetic nervous system.

19. The method of claim 18, wherein applying energy to the portion of parasympathetic nervous system comprises applying thermal energy, microwave, electrical energy, cryogenic energy, acoustic energy, radio frequency energy, pulsed high voltage energy, mechanical energy, ionizing radiation, or optical energy to the portion of the parasympathetic nervous system.

20. The method of claim 18, wherein applying energy to the portion of parasympathetic nervous system does not cause permanent damage to any interior airway walls of the patient.

21. The method of claim 18, further comprising protecting an interior airway wall of the patient from permanent damage while applying the energy.

22. The method of claim 2, wherein the nerve trunk is damaged by delivering energy from an interventional device.

23. The method of claim 22, wherein the energy is delivered from within the airway.

24. The method of claim 22, wherein the energy is delivered from outside the airway.

25. The method of claim 2, wherein the denervation procedure prevents the acetylcholine from influencing postjunctional activities by inhibiting binding of acetylcholine to receptor sites in nerve cells.

26. The method of claim 25, wherein the receptor sites comprise muscarinic (M) receptors.

* * * * *